(12) United States Patent
DeCarlo et al.

(10) Patent No.: US 7,488,719 B1
(45) Date of Patent: *Feb. 10, 2009

(54) WOUND AND CUTANEOUS INJURY HEALING WITH A NUCLEIC ACID ENCODING PERLECAN

(75) Inventors: Arthur A. DeCarlo, Weston, FL (US); John Whitelock, Sydney (AU)

(73) Assignee: Agenta Biotechnologies, Inc., Birmingham, AL (US)

( * ) Notice: Subject to any disclaimer, the term of this patent is extended or adjusted under 35 U.S.C. 154(b) by 253 days.

This patent is subject to a terminal disclaimer.

(21) Appl. No.: 11/604,633

(22) Filed: Nov. 27, 2006

Related U.S. Application Data

(63) Continuation of application No. 10/420,270, filed on Apr. 22, 2003, now Pat. No. 7,141,551.

(60) Provisional application No. 60/374,553, filed on Apr. 22, 2002.

(51) Int. Cl.
*A01K 63/00* (2006.01)
*A61K 48/00* (2006.01)

(52) U.S. Cl. ................ 514/44; 424/93.2; 424/93.21

(58) Field of Classification Search ............ None
See application file for complete search history.

(56) References Cited

U.S. PATENT DOCUMENTS

| 6,524,573 | B1 | 2/2003 | Iozzo |
| 7,029,668 | B2 | 4/2006 | Simons |
| 7,141,551 | B1 | 11/2006 | DeCarlo |

FOREIGN PATENT DOCUMENTS

| WO | WO 99/06054 | 2/1999 |

OTHER PUBLICATIONS

Groffen et al. Expression and Characterization of Human Perlecan Domains I and II Syntesized by Baculovirus-Infected instect Cells. Eur.J. Biochem. 241, pp. 827-834, 1996.
Nugent et al. Fibroblast Growth Factor-2. International J. Biochem. Cell Viol. 2000, vol. 32 pp. 115-120.
Zhao,e al Adenovirus-Mediated Decorin Gene Transfer Prevents TGF-Beta Induced Inhibition of Lung Morphogenesis. American.J. Physiol., vol. 277(Lung Cell. Mol. Phys.21) pL412-422, 1999.
International Application, WO 02/17955 A1, Mar. 7, 2002.

*Primary Examiner*—Deborah Crouch
(74) *Attorney, Agent, or Firm*—Bradley Arant Boult Cummings, LLP

(57) ABSTRACT

A description of a biomolecule named Perlecan which is added internally or topically, or is expressed from exogenously added nucleic acids, as a whole or in part, to a healing wound to improve the success of wound healing is disclosed. Relevant embodiments for this patent technology are described.

15 Claims, No Drawings

SEQUENCE LISTING

```
<160> NUMBER OF SEQ ID NOS: 5

<210> SEQ ID NO 1
<211> LENGTH: 13
<212> TYPE: PRT
<213> ORGANISM: Homo sapiens

<400> SEQUENCE: 1

Leu Pro Ala Ser Phe Arg Gly Asp Lys Val Thr Ser Tyr
1               5                   10

<210> SEQ ID NO 2
<211> LENGTH: 6
<212> TYPE: PRT
<213> ORGANISM: Homo sapiens

<400> SEQUENCE: 2

Gly Arg Gly Asp Ser Pro
1               5
```

<210> SEQ ID NO 3
<211> LENGTH: 6
<212> TYPE: PRT
<213> ORGANISM: Homo sapiens

<400> SEQUENCE: 3

```
Gly Arg Gly Glu Ser Pro
1               5
```

<210> SEQ ID NO 4
<211> LENGTH: 4391
<212> TYPE: PRT
<213> ORGANISM: Homo sapiens

<400> SEQUENCE: 4

```
Met Gly Trp Arg Ala Pro Gly Ala Leu Leu Ala Leu Leu Leu His
1               5                   10                  15

Gly Arg Leu Leu Ala Val Thr His Gly Leu Arg Ala Tyr Asp Gly Leu
                20                  25                  30

Ser Leu Pro Glu Asp Ile Glu Thr Val Thr Ala Ser Gln Met Arg Trp
            35                  40                  45

Thr His Ser Tyr Leu Ser Asp Asp Glu Tyr Met Leu Ala Asp Ser Ile
        50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
        130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
        210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Val Thr His Ala Pro
            260                 265                 270

Gln Pro Leu Leu Pro Gly Ser Val Arg Pro Leu Pro Cys Gly Pro Gln
        275                 280                 285

Glu Ala Ala Cys Arg Asn Gly His Cys Ile Pro Arg Asp Tyr Leu Cys
        290                 295                 300

Asp Gly Gln Glu Asp Cys Glu Asp Gly Ser Asp Glu Leu Asp Cys Gly
305                 310                 315                 320
```

-continued

Pro Pro Pro Pro Cys Glu Pro Asn Glu Phe Pro Cys Gly Asn Gly His
            325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
            355                 360                 365

Gly Pro Thr Gln Phe Arg Cys Val Ser Thr Asn Met Cys Ile Pro Ala
            370                 375                 380

Ser Phe His Cys Asp Glu Ser Asp Cys Pro Asp Arg Ser Asp Glu
385                 390                 395                 400

Phe Gly Cys Met Pro Pro Gln Val Val Thr Pro Pro Arg Glu Ser Ile
                405                 410                 415

Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
            435                 440                 445

Ser His Pro Arg Val Thr Val Thr Ser Glu Gly Gly Arg Gly Thr Leu
    450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
        515                 520                 525

Val Cys Gln Ser Thr Arg Arg Phe Arg Asp Gln Ile Arg Leu Arg Phe
            530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
            565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
            595                 600                 605

Ser Tyr Gly Gly Ser Leu Arg Tyr Asn Val Arg Tyr Glu Leu Ala Arg
    610                 615                 620

Gly Met Leu Glu Pro Val Gln Arg Pro Asp Val Val Leu Val Gly Ala
625                 630                 635                 640

Gly Tyr Arg Leu Leu Ser Arg Gly His Thr Pro Thr Gln Pro Gly Ala
            645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
            675                 680                 685

Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
            725                 730                 735

```
Tyr Ser Gly Leu Ser Cys Glu Ser Cys Asp Ala His Phe Thr Arg Val
            740                 745                 750
Pro Gly Gly Pro Tyr Leu Gly Thr Cys Ser Gly Cys Ser Cys Asn Gly
            755                 760                 765
His Ala Ser Ser Cys Asp Pro Val Tyr Gly His Cys Leu Asn Cys Gln
    770                 775                 780
His Asn Thr Glu Gly Pro Gln Cys Asn Lys Cys Lys Ala Gly Phe Phe
785                 790                 795                 800
Gly Asp Ala Met Lys Ala Thr Ala Thr Ser Cys Arg Pro Cys Pro Cys
                805                 810                 815
Pro Tyr Ile Asp Ala Ser Arg Arg Phe Ser Asp Thr Cys Phe Leu Asp
            820                 825                 830
Thr Asp Gly Gln Ala Thr Cys Asp Ala Cys Ala Pro Gly Tyr Thr Gly
            835                 840                 845
Arg Arg Cys Glu Ser Cys Ala Pro Gly Tyr Glu Gly Asn Pro Ile Gln
850                 855                 860
Pro Gly Gly Lys Cys Arg Pro Val Asn Gln Glu Ile Val Arg Cys Asp
865                 870                 875                 880
Glu Arg Gly Ser Met Gly Thr Ser Gly Glu Ala Cys Arg Cys Lys Asn
                885                 890                 895
Asn Val Val Gly Arg Leu Cys Asn Glu Cys Ala Asp Gly Ser Phe His
            900                 905                 910
Leu Ser Thr Arg Asn Pro Asp Gly Cys Leu Lys Cys Phe Cys Met Gly
            915                 920                 925
Val Ser Arg His Cys Thr Ser Ser Ser Trp Ser Arg Ala Gln Leu His
    930                 935                 940
Gly Ala Ser Glu Glu Pro Gly His Phe Ser Leu Thr Asn Ala Ala Ser
945                 950                 955                 960
Thr His Thr Thr Asn Glu Gly Ile Phe Ser Pro Thr Pro Gly Glu Leu
                965                 970                 975
Gly Phe Ser Ser Phe His Arg Leu Leu Ser Gly Pro Tyr Phe Trp Ser
            980                 985                 990
Leu Pro Ser Arg Phe Leu Gly Asp Lys Val Thr Ser Tyr Gly Gly Glu
            995                 1000                1005
Leu Arg Phe Thr Val Thr Gln Arg Ser Gln Pro Gly Ser Thr Pro
    1010                1015                1020
Leu His Gly Gln Pro Leu Val Val Leu Gln Gly Asn Asn Ile Ile
    1025                1030                1035
Leu Glu His His Val Ala Gln Glu Pro Ser Pro Gly Gln Pro Ser
    1040                1045                1050
Thr Phe Ile Val Pro Phe Arg Glu Gln Ala Trp Gln Arg Pro Asp
    1055                1060                1065
Gly Gln Pro Ala Thr Arg Glu His Leu Leu Met Ala Leu Ala Gly
    1070                1075                1080
Ile Asp Thr Leu Leu Ile Arg Ala Ser Tyr Ala Gln Gln Pro Ala
    1085                1090                1095
Glu Ser Arg Val Ser Gly Ile Ser Met Asp Val Ala Val Pro Glu
    1100                1105                1110
Glu Thr Gly Gln Asp Pro Ala Leu Glu Val Glu Gln Cys Ser Cys
    1115                1120                1125
Pro Pro Gly Tyr Arg Gly Pro Ser Cys Gln Asp Cys Asp Thr Gly
    1130                1135                1140
Tyr Thr Arg Thr Pro Ser Gly Leu Tyr Leu Gly Thr Cys Glu Arg
```

-continued

```
              1145                1150                1155
Cys  Ser  Cys  His  Gly  His  Ser  Glu  Ala  Cys  Glu  Pro  Glu  Thr  Gly
              1160                1165                1170
Ala  Cys  Gln  Gly  Cys  Gln  His  His  Thr  Glu  Gly  Pro  Arg  Cys  Glu
              1175                1180                1185
Gln  Cys  Gln  Pro  Gly  Tyr  Tyr  Gly  Asp  Ala  Gln  Arg  Gly  Thr  Pro
              1190                1195                1200
Gln  Asp  Cys  Gln  Leu  Cys  Pro  Cys  Tyr  Gly  Asp  Pro  Ala  Ala  Gly
              1205                1210                1215
Gln  Ala  Ala  His  Thr  Cys  Phe  Leu  Asp  Thr  Asp  Gly  His  Pro  Thr
              1220                1225                1230
Cys  Asp  Ala  Cys  Ser  Pro  Gly  His  Ser  Gly  Arg  His  Cys  Glu  Arg
              1235                1240                1245
Cys  Ala  Pro  Gly  Tyr  Tyr  Gly  Asn  Pro  Ser  Gln  Gly  Gln  Pro  Cys
              1250                1255                1260
Gln  Arg  Asp  Ser  Gln  Val  Pro  Gly  Pro  Ile  Gly  Cys  Asn  Cys  Asp
              1265                1270                1275
Pro  Gln  Gly  Ser  Val  Ser  Ser  Gln  Cys  Asp  Ala  Ala  Gly  Gln  Cys
              1280                1285                1290
Gln  Cys  Lys  Ala  Gln  Val  Glu  Gly  Leu  Thr  Cys  Ser  His  Cys  Arg
              1295                1300                1305
Pro  His  His  Phe  His  Leu  Ser  Ala  Ser  Asn  Pro  Asp  Gly  Cys  Leu
              1310                1315                1320
Pro  Cys  Phe  Cys  Met  Gly  Ile  Thr  Gln  Gln  Cys  Ala  Ser  Ser  Ala
              1325                1330                1335
Tyr  Thr  Arg  His  Leu  Ile  Ser  Thr  His  Phe  Ala  Pro  Gly  Asp  Phe
              1340                1345                1350
Gln  Gly  Phe  Ala  Leu  Val  Asn  Pro  Gln  Arg  Asn  Ser  Arg  Leu  Thr
              1355                1360                1365
Gly  Glu  Phe  Thr  Val  Glu  Pro  Val  Pro  Glu  Gly  Ala  Gln  Leu  Ser
              1370                1375                1380
Phe  Gly  Asn  Phe  Ala  Gln  Leu  Gly  His  Glu  Ser  Phe  Tyr  Trp  Gln
              1385                1390                1395
Leu  Pro  Glu  Thr  Tyr  Gln  Gly  Asp  Lys  Val  Ala  Ala  Tyr  Gly  Gly
              1400                1405                1410
Lys  Leu  Arg  Tyr  Thr  Leu  Ser  Tyr  Thr  Ala  Gly  Pro  Gln  Gly  Ser
              1415                1420                1425
Pro  Leu  Ser  Asp  Pro  Asp  Val  Gln  Ile  Thr  Gly  Asn  Asn  Ile  Met
              1430                1435                1440
Leu  Val  Ala  Ser  Gln  Pro  Ala  Leu  Gln  Gly  Pro  Glu  Arg  Arg  Ser
              1445                1450                1455
Tyr  Glu  Ile  Met  Phe  Arg  Glu  Glu  Phe  Trp  Arg  Arg  Pro  Asp  Gly
              1460                1465                1470
Gln  Pro  Ala  Thr  Arg  Glu  His  Leu  Leu  Met  Ala  Leu  Ala  Asp  Leu
              1475                1480                1485
Asp  Glu  Leu  Leu  Ile  Arg  Ala  Thr  Phe  Ser  Ser  Val  Pro  Leu  Val
              1490                1495                1500
Ala  Ser  Ile  Ser  Ala  Val  Ser  Leu  Glu  Val  Ala  Gln  Pro  Gly  Pro
              1505                1510                1515
Ser  Asn  Arg  Pro  Arg  Ala  Leu  Glu  Val  Glu  Glu  Cys  Arg  Cys  Pro
              1520                1525                1530
Pro  Gly  Tyr  Ile  Gly  Leu  Ser  Cys  Gln  Asp  Cys  Ala  Pro  Gly  Tyr
              1535                1540                1545
```

-continued

```
Thr Arg Thr Gly Ser Gly Leu Tyr Leu Gly His Cys Glu Leu Cys
1550                1555                1560

Glu Cys Asn Gly His Ser Asp Leu Cys His Pro Glu Thr Gly Ala
1565                1570                1575

Cys Ser Gln Cys Gln His Asn Ala Ala Gly Glu Phe Cys Glu Leu
1580                1585                1590

Cys Ala Pro Gly Tyr Tyr Gly Asp Ala Thr Ala Gly Thr Pro Glu
1595                1600                1605

Asp Cys Gln Pro Cys Ala Cys Pro Leu Thr Asn Pro Glu Asn Met
1610                1615                1620

Phe Ser Arg Thr Cys Glu Ser Leu Gly Ala Gly Gly Tyr Arg Cys
1625                1630                1635

Thr Ala Cys Glu Pro Gly Tyr Thr Gly Gln Tyr Cys Glu Gln Cys
1640                1645                1650

Gly Pro Gly Tyr Val Gly Asn Pro Ser Val Gln Gly Gly Gln Cys
1655                1660                1665

Leu Pro Glu Thr Asn Gln Ala Pro Leu Val Val Glu Val His Pro
1670                1675                1680

Ala Arg Ser Ile Val Pro Gln Gly Gly Ser His Ser Leu Arg Cys
1685                1690                1695

Gln Val Ser Gly Ser Pro Pro His Tyr Phe Tyr Trp Ser Arg Glu
1700                1705                1710

Asp Gly Arg Pro Val Pro Ser Gly Thr Gln Gln Arg His Gln Gly
1715                1720                1725

Ser Glu Leu His Phe Pro Ser Val Gln Pro Ser Asp Ala Gly Val
1730                1735                1740

Tyr Ile Cys Thr Cys Arg Asn Leu His Gln Ser Asn Thr Ser Arg
1745                1750                1755

Ala Glu Leu Leu Val Thr Glu Ala Pro Ser Lys Pro Ile Thr Val
1760                1765                1770

Thr Val Glu Glu Gln Arg Ser Gln Ser Val Arg Pro Gly Ala Asp
1775                1780                1785

Val Thr Phe Ile Cys Thr Ala Lys Ser Lys Ser Pro Ala Tyr Thr
1790                1795                1800

Leu Val Trp Thr Arg Leu His Asn Gly Lys Leu Pro Thr Arg Ala
1805                1810                1815

Met Asp Phe Asn Gly Ile Leu Thr Ile Arg Asn Val Gln Leu Ser
1820                1825                1830

Asp Ala Gly Thr Tyr Val Cys Thr Gly Ser Asn Met Phe Ala Met
1835                1840                1845

Asp Gln Gly Thr Ala Thr Leu His Val Gln Ala Ser Gly Thr Leu
1850                1855                1860

Ser Ala Pro Val Val Ser Ile His Pro Pro Gln Leu Thr Val Gln
1865                1870                1875

Pro Gly Gln Leu Ala Glu Phe Arg Cys Ser Ala Thr Gly Ser Pro
1880                1885                1890

Thr Pro Thr Leu Glu Trp Thr Gly Gly Pro Gly Gly Gln Leu Pro
1895                1900                1905

Ala Lys Ala Gln Ile His Gly Gly Ile Leu Arg Leu Pro Ala Val
1910                1915                1920

Glu Pro Thr Asp Gln Ala Gln Tyr Leu Cys Arg Ala His Ser Ser
1925                1930                1935
```

-continued

Ala Gly Gln Gln Val Ala Arg Ala Val Leu His Val His Gly Gly
    1940                1945                1950

Gly Gly Pro Arg Val Gln Val Ser Pro Glu Arg Thr Gln Val His
    1955                1960                1965

Ala Gly Arg Thr Val Arg Leu Tyr Cys Arg Ala Ala Gly Val Pro
    1970                1975                1980

Ser Ala Thr Ile Thr Trp Arg Lys Glu Gly Gly Ser Leu Pro Pro
    1985                1990                1995

Gln Ala Arg Ser Glu Arg Thr Asp Ile Ala Thr Leu Leu Ile Pro
    2000                2005                2010

Ala Ile Thr Thr Ala Asp Ala Gly Phe Tyr Leu Cys Val Ala Thr
    2015                2020                2025

Ser Pro Ala Gly Thr Ala Gln Ala Arg Met Gln Val Val Val Leu
    2030                2035                2040

Ser Ala Ser Asp Ala Ser Pro Pro Gly Val Lys Ile Glu Ser Ser
    2045                2050                2055

Ser Pro Ser Val Thr Glu Gly Gln Thr Leu Asp Leu Asn Cys Val
    2060                2065                2070

Val Ala Gly Ser Ala His Ala Gln Val Thr Trp Tyr Arg Arg Gly
    2075                2080                2085

Gly Ser Leu Pro Pro His Thr Gln Val His Gly Ser Arg Leu Arg
    2090                2095                2100

Leu Pro Gln Val Ser Pro Ala Asp Ser Gly Glu Tyr Val Cys Arg
    2105                2110                2115

Val Glu Asn Gly Ser Gly Pro Lys Glu Ala Ser Ile Thr Val Ser
    2120                2125                2130

Val Leu His Gly Thr His Ser Gly Pro Ser Tyr Thr Pro Val Pro
    2135                2140                2145

Gly Ser Thr Arg Pro Ile Arg Ile Glu Pro Ser Ser Ser His Val
    2150                2155                2160

Ala Glu Gly Gln Thr Leu Asp Leu Asn Cys Val Val Pro Gly Gln
    2165                2170                2175

Ala His Ala Gln Val Thr Trp His Lys Arg Gly Gly Ser Leu Pro
    2180                2185                2190

Ala Arg His Gln Thr His Gly Ser Leu Leu Arg Leu His Gln Val
    2195                2200                2205

Thr Pro Ala Asp Ser Gly Glu Tyr Val Cys His Val Val Gly Thr
    2210                2215                2220

Ser Gly Pro Leu Glu Ala Ser Val Leu Val Thr Ile Glu Ala Ser
    2225                2230                2235

Val Ile Pro Gly Pro Ile Pro Pro Val Arg Ile Glu Ser Ser Ser
    2240                2245                2250

Ser Thr Val Ala Glu Gly Gln Thr Leu Asp Leu Ser Cys Val Val
    2255                2260                2265

Ala Gly Gln Ala His Ala Gln Val Thr Trp Tyr Lys Arg Gly Gly
    2270                2275                2280

Ser Leu Pro Ala Arg His Gln Val Arg Gly Ser Arg Leu Tyr Ile
    2285                2290                2295

Phe Gln Ala Ser Pro Ala Asp Ala Gly Gln Tyr Val Cys Arg Ala
    2300                2305                2310

Ser Asn Gly Met Glu Ala Ser Ile Thr Val Thr Val Thr Gly Thr
    2315                2320                2325

Gln Gly Ala Asn Leu Ala Tyr Pro Ala Gly Ser Thr Gln Pro Ile

-continued

```
              2330                2335                2340
Arg Ile Glu Pro Ser Ser Ser Gln Val Ala Glu Gly Gln Thr Leu
        2345                2350                2355
Asp Leu Asn Cys Val Val Pro Gly Gln Ser His Ala Gln Val Thr
        2360                2365                2370
Trp His Lys Arg Gly Gly Ser Leu Pro Val Arg His Gln Thr His
        2375                2380                2385
Gly Ser Leu Leu Arg Leu Tyr Gln Ala Ser Pro Ala Asp Ser Gly
        2390                2395                2400
Glu Tyr Val Cys Arg Val Leu Gly Ser Ser Val Pro Leu Glu Ala
        2405                2410                2415
Ser Val Leu Val Thr Ile Glu Pro Ala Gly Ser Val Pro Ala Leu
        2420                2425                2430
Gly Val Thr Pro Thr Val Arg Ile Glu Ser Ser Ser Ser Gln Val
        2435                2440                2445
Ala Glu Gly Gln Thr Leu Asp Leu Asn Cys Leu Val Ala Gly Gln
        2450                2455                2460
Ala His Ala Gln Val Thr Trp His Lys Arg Gly Gly Ser Leu Pro
        2465                2470                2475
Ala Arg His Gln Val His Gly Ser Arg Leu Arg Leu Leu Gln Val
        2480                2485                2490
Thr Pro Ala Asp Ser Gly Glu Tyr Val Cys Arg Val Val Gly Ser
        2495                2500                2505
Ser Gly Thr Gln Glu Ala Ser Val Leu Val Thr Ile Gln Gln Arg
        2510                2515                2520
Leu Ser Gly Ser His Ser Gln Gly Val Ala Tyr Pro Val Arg Ile
        2525                2530                2535
Glu Ser Ser Ser Ala Ser Leu Ala Asn Gly His Thr Leu Asp Leu
        2540                2545                2550
Asn Cys Leu Val Ala Ser Gln Ala Pro His Thr Ile Thr Trp Tyr
        2555                2560                2565
Lys Arg Gly Gly Ser Leu Pro Ser Arg His Gln Ile Val Gly Ser
        2570                2575                2580
Arg Leu Arg Ile Pro Gln Val Thr Pro Ala Asp Ser Gly Glu Tyr
        2585                2590                2595
Val Cys His Val Ser Asn Gly Ala Gly Ser Arg Glu Thr Ser Leu
        2600                2605                2610
Ile Val Thr Ile Gln Gly Ser Gly Ser Ser His Val Pro Ser Val
        2615                2620                2625
Ser Pro Pro Ile Arg Ile Glu Ser Ser Ser Pro Thr Val Val Glu
        2630                2635                2640
Gly Gln Thr Leu Asp Leu Asn Cys Val Val Ala Arg Gln Pro Gln
        2645                2650                2655
Ala Ile Ile Thr Trp Tyr Lys Arg Gly Gly Ser Leu Pro Ser Arg
        2660                2665                2670
His Gln Thr His Gly Ser His Leu Arg Leu His Gln Met Ser Val
        2675                2680                2685
Ala Asp Ser Gly Glu Tyr Val Cys Arg Ala Asn Asn Asn Ile Asp
        2690                2695                2700
Ala Leu Glu Ala Ser Ile Val Ile Ser Val Ser Pro Ser Ala Gly
        2705                2710                2715
Ser Pro Ser Ala Pro Gly Ser Ser Met Pro Ile Arg Ile Glu Ser
        2720                2725                2730
```

-continued

```
Ser Ser Ser His Val Ala Glu Gly Glu Thr Leu Asp Leu Asn Cys
    2735            2740            2745

Val Val Pro Gly Gln Ala His Ala Gln Val Thr Trp His Lys Arg
    2750            2755            2760

Gly Gly Ser Leu Pro Ser His His Gln Thr Arg Gly Ser Arg Leu
    2765            2770            2775

Arg Leu His His Val Ser Pro Ala Asp Ser Gly Glu Tyr Val Cys
    2780            2785            2790

Arg Val Met Gly Ser Ser Gly Pro Leu Glu Ala Ser Val Leu Val
    2795            2800            2805

Thr Ile Glu Ala Ser Gly Ser Ser Ala Val His Val Pro Ala Pro
    2810            2815            2820

Gly Gly Ala Pro Pro Ile Arg Ile Glu Pro Ser Ser Ser Arg Val
    2825            2830            2835

Ala Glu Gly Gln Thr Leu Asp Leu Lys Cys Val Val Pro Gly Gln
    2840            2845            2850

Ala His Ala Gln Val Thr Trp His Lys Arg Gly Gly Asn Leu Pro
    2855            2860            2865

Ala Arg His Gln Val His Gly Pro Leu Leu Arg Leu Asn Gln Val
    2870            2875            2880

Ser Pro Ala Asp Ser Gly Glu Tyr Ser Cys Gln Val Thr Gly Ser
    2885            2890            2895

Ser Gly Thr Leu Glu Ala Ser Val Leu Val Thr Ile Glu Pro Ser
    2900            2905            2910

Ser Pro Gly Pro Ile Pro Ala Pro Gly Leu Ala Gln Pro Ile Tyr
    2915            2920            2925

Ile Glu Ala Ser Ser Ser His Val Thr Glu Gly Gln Thr Leu Asp
    2930            2935            2940

Leu Asn Cys Val Val Pro Gly Gln Ala His Ala Gln Val Thr Trp
    2945            2950            2955

Tyr Lys Arg Gly Gly Ser Leu Pro Ala Arg His Gln Thr His Gly
    2960            2965            2970

Ser Gln Leu Arg Leu His Leu Val Ser Pro Ala Asp Ser Gly Glu
    2975            2980            2985

Tyr Val Cys Arg Ala Ala Ser Gly Pro Gly Pro Glu Gln Glu Ala
    2990            2995            3000

Ser Phe Thr Val Thr Val Pro Pro Ser Glu Gly Ser Ser Tyr Arg
    3005            3010            3015

Leu Arg Ser Pro Val Ile Ser Ile Asp Pro Pro Ser Ser Thr Val
    3020            3025            3030

Gln Gln Gly Gln Asp Ala Ser Phe Lys Cys Leu Ile His Asp Gly
    3035            3040            3045

Ala Ala Pro Ile Ser Leu Glu Trp Lys Thr Arg Asn Gln Glu Leu
    3050            3055            3060

Glu Asp Asn Val His Ile Ser Pro Asn Gly Ser Ile Ile Thr Ile
    3065            3070            3075

Val Gly Thr Arg Pro Ser Asn His Gly Thr Tyr Arg Cys Val Ala
    3080            3085            3090

Ser Asn Ala Tyr Gly Val Ala Gln Ser Val Val Asn Leu Ser Val
    3095            3100            3105

His Gly Pro Pro Thr Val Ser Val Leu Pro Glu Gly Pro Val Trp
    3110            3115            3120
```

-continued

```
Val Lys Val Gly Lys Ala Val Thr Leu Glu Cys Val Ser Ala Gly
    3125            3130                3135

Glu Pro Arg Ser Ser Ala Arg Trp Thr Arg Ile Ser Ser Thr Pro
    3140            3145                3150

Ala Lys Leu Glu Gln Arg Thr Tyr Gly Leu Met Asp Ser His Ala
    3155            3160                3165

Val Leu Gln Ile Ser Ser Ala Lys Pro Ser Asp Ala Gly Thr Tyr
    3170            3175                3180

Val Cys Leu Ala Gln Asn Ala Leu Gly Thr Ala Gln Lys Gln Val
    3185            3190                3195

Glu Val Ile Val Asp Thr Gly Ala Met Ala Pro Gly Ala Pro Gln
    3200            3205                3210

Val Gln Ala Glu Glu Ala Glu Leu Thr Val Glu Ala Gly His Thr
    3215            3220                3225

Ala Thr Leu Arg Cys Ser Ala Thr Gly Ser Pro Ala Pro Thr Ile
    3230            3235                3240

His Trp Ser Lys Leu Arg Ser Pro Leu Pro Trp Gln His Arg Leu
    3245            3250                3255

Glu Gly Asp Thr Leu Ile Ile Pro Arg Val Ala Gln Gln Asp Ser
    3260            3265                3270

Gly Gln Tyr Ile Cys Asn Ala Thr Ser Pro Ala Gly His Ala Glu
    3275            3280                3285

Ala Thr Ile Ile Leu His Val Glu Ser Pro Pro Tyr Ala Thr Thr
    3290            3295                3300

Val Pro Glu His Ala Ser Val Gln Ala Gly Glu Thr Val Gln Leu
    3305            3310                3315

Gln Cys Leu Ala His Gly Thr Pro Pro Leu Thr Phe Gln Trp Ser
    3320            3325                3330

Arg Val Gly Ser Ser Leu Pro Gly Arg Ala Thr Ala Arg Asn Glu
    3335            3340                3345

Leu Leu His Phe Glu Arg Ala Ala Pro Glu Asp Ser Gly Arg Tyr
    3350            3355                3360

Arg Cys Arg Val Thr Asn Lys Val Gly Ser Ala Glu Ala Phe Ala
    3365            3370                3375

Gln Leu Leu Val Gln Gly Pro Pro Gly Ser Leu Pro Ala Thr Ser
    3380            3385                3390

Ile Pro Ala Gly Ser Thr Pro Thr Val Gln Val Thr Pro Gln Leu
    3395            3400                3405

Glu Thr Lys Ser Ile Gly Ala Ser Val Glu Phe His Cys Ala Val
    3410            3415                3420

Pro Ser Asp Gln Gly Thr Gln Leu Arg Trp Phe Lys Glu Gly Gly
    3425            3430                3435

Gln Leu Pro Pro Gly His Ser Val Gln Asp Gly Val Leu Arg Ile
    3440            3445                3450

Gln Asn Leu Asp Gln Ser Cys Gln Gly Thr Tyr Ile Cys Gln Ala
    3455            3460                3465

His Gly Pro Trp Gly Lys Ala Gln Ala Ser Ala Gln Leu Val Ile
    3470            3475                3480

Gln Ala Leu Pro Ser Val Leu Ile Asn Ile Arg Thr Ser Val Gln
    3485            3490                3495

Thr Val Val Val Gly His Ala Val Glu Phe Glu Cys Leu Ala Leu
    3500            3505                3510

Gly Asp Pro Lys Pro Gln Val Thr Trp Ser Lys Val Gly Gly His
```

-continued

```
          3515                3520                3525
Leu Arg Pro Gly Ile Val Gln Ser Gly Gly Val Val Arg Ile Ala
        3530                3535                3540
His Val Glu Leu Ala Asp Ala Gly Gln Tyr Arg Cys Thr Ala Thr
        3545                3550                3555
Asn Ala Ala Gly Thr Thr Gln Ser His Val Leu Leu Leu Val Gln
        3560                3565                3570
Ala Leu Pro Gln Ile Ser Met Pro Gln Glu Val Arg Val Pro Ala
        3575                3580                3585
Gly Ser Ala Ala Val Phe Pro Cys Ile Ala Ser Gly Tyr Pro Thr
        3590                3595                3600
Pro Asp Ile Ser Trp Ser Lys Leu Asp Gly Ser Leu Pro Pro Asp
        3605                3610                3615
Ser Arg Leu Glu Asn Asn Met Leu Met Leu Pro Ser Val Arg Pro
        3620                3625                3630
Gln Asp Ala Gly Thr Tyr Val Cys Thr Ala Thr Asn Arg Gln Gly
        3635                3640                3645
Lys Val Lys Ala Phe Ala His Leu Gln Val Pro Glu Arg Val Val
        3650                3655                3660
Pro Tyr Phe Thr Gln Thr Pro Tyr Ser Phe Leu Pro Leu Pro Thr
        3665                3670                3675
Ile Lys Asp Ala Tyr Arg Lys Phe Glu Ile Lys Ile Thr Phe Arg
        3680                3685                3690
Pro Asp Ser Ala Asp Gly Met Leu Leu Tyr Asn Gly Gln Lys Arg
        3695                3700                3705
Val Pro Gly Ser Pro Thr Asn Leu Ala Asn Arg Gln Pro Asp Phe
        3710                3715                3720
Ile Ser Phe Gly Leu Val Gly Gly Arg Pro Glu Phe Arg Phe Asp
        3725                3730                3735
Ala Gly Ser Gly Met Ala Thr Ile Arg His Pro Thr Pro Leu Ala
        3740                3745                3750
Leu Gly His Phe His Thr Val Thr Leu Leu Arg Ser Leu Thr Gln
        3755                3760                3765
Gly Ser Leu Ile Val Gly Asp Leu Ala Pro Val Asn Gly Thr Ser
        3770                3775                3780
Gln Gly Lys Phe Gln Gly Leu Asp Leu Asn Glu Glu Leu Tyr Leu
        3785                3790                3795
Gly Gly Tyr Pro Asp Tyr Gly Ala Ile Pro Lys Ala Gly Leu Ser
        3800                3805                3810
Ser Gly Phe Ile Gly Cys Val Arg Glu Leu Arg Ile Gln Gly Glu
        3815                3820                3825
Glu Ile Val Phe His Asp Leu Asn Leu Thr Ala His Gly Ile Ser
        3830                3835                3840
His Cys Pro Thr Cys Arg Asp Arg Pro Cys Gln Asn Gly Gly Gln
        3845                3850                3855
Cys His Asp Ser Glu Ser Ser Tyr Val Cys Val Cys Pro Ala
        3860                3865                3870
Gly Phe Thr Gly Ser Arg Cys Glu His Ser Gln Ala Leu His Cys
        3875                3880                3885
His Pro Glu Ala Cys Gly Pro Asp Ala Thr Cys Val Asn Arg Pro
        3890                3895                3900
Asp Gly Arg Gly Tyr Thr Cys Arg Cys His Leu Gly Arg Ser Gly
        3905                3910                3915
```

-continued

Leu Arg Cys Glu Glu Gly Val Thr Val Thr Thr Pro Ser Leu Ser
    3920            3925            3930

Gly Ala Gly Ser Tyr Leu Ala Leu Pro Ala Leu Thr Asn Thr His
    3935            3940            3945

His Glu Leu Arg Leu Asp Val Glu Phe Lys Pro Leu Ala Pro Asp
    3950            3955            3960

Gly Val Leu Leu Phe Ser Gly Gly Lys Ser Gly Pro Val Glu Asp
    3965            3970            3975

Phe Val Ser Leu Ala Met Val Gly Gly His Leu Glu Phe Arg Tyr
    3980            3985            3990

Glu Leu Gly Ser Gly Leu Ala Val Leu Arg Ser Ala Glu Pro Leu
    3995            4000            4005

Ala Leu Gly Arg Trp His Arg Val Ser Ala Glu Arg Leu Asn Lys
    4010            4015            4020

Asp Gly Ser Leu Arg Val Asn Gly Gly Arg Pro Val Leu Arg Ser
    4025            4030            4035

Ser Pro Gly Lys Ser Gln Gly Leu Asn Leu His Thr Leu Leu Tyr
    4040            4045            4050

Leu Gly Gly Val Glu Pro Ser Val Pro Leu Ser Pro Ala Thr Asn
    4055            4060            4065

Met Ser Ala His Phe Arg Gly Cys Val Gly Glu Val Ser Val Asn
    4070            4075            4080

Gly Lys Arg Leu Asp Leu Thr Tyr Ser Phe Leu Gly Ser Gln Gly
    4085            4090            4095

Ile Gly Gln Cys Tyr Asp Ser Ser Pro Cys Glu Arg Gln Pro Cys
    4100            4105            4110

Gln His Gly Ala Thr Cys Met Pro Ala Gly Glu Tyr Glu Phe Gln
    4115            4120            4125

Cys Leu Cys Arg Asp Gly Phe Lys Gly Asp Leu Cys Glu His Glu
    4130            4135            4140

Glu Asn Pro Cys Gln Leu Arg Glu Pro Cys Leu His Gly Gly Thr
    4145            4150            4155

Cys Gln Gly Thr Arg Cys Leu Cys Leu Pro Gly Phe Ser Gly Pro
    4160            4165            4170

Arg Cys Gln Gln Gly Ser Gly His Gly Ile Ala Glu Ser Asp Trp
    4175            4180            4185

His Leu Glu Gly Ser Gly Gly Asn Asp Ala Pro Gly Gln Tyr Gly
    4190            4195            4200

Ala Tyr Phe His Asp Asp Gly Phe Leu Ala Phe Pro Gly His Val
    4205            4210            4215

Phe Ser Arg Ser Leu Pro Glu Val Pro Glu Thr Ile Glu Leu Glu
    4220            4225            4230

Val Arg Thr Ser Thr Ala Ser Gly Leu Leu Leu Trp Gln Gly Val
    4235            4240            4245

Glu Val Gly Glu Ala Gly Gln Gly Lys Asp Phe Ile Ser Leu Gly
    4250            4255            4260

Leu Gln Asp Gly His Leu Val Phe Arg Tyr Gln Leu Gly Ser Gly
    4265            4270            4275

Glu Ala Arg Leu Val Ser Glu Asp Pro Ile Asn Asp Gly Glu Trp
    4280            4285            4290

His Arg Val Thr Ala Leu Arg Glu Gly Arg Arg Gly Ser Ile Gln
    4295            4300            4305

-continued

| Val | Asp | Gly | Glu | Glu | Leu | Val | Ser | Gly | Arg | Ser | Gly | Pro | Asn |
| | 4310 | | | | 4315 | | | | 4320 | | | | |

| Val | Ala | Val | Asn | Ala | Lys | Gly | Ser | Val | Tyr | Ile | Gly | Gly | Ala | Pro |
| | 4325 | | | | 4330 | | | | 4335 | | | | | |

| Asp | Val | Ala | Thr | Leu | Thr | Gly | Gly | Arg | Phe | Ser | Ser | Gly | Ile | Thr |
| | 4340 | | | | 4345 | | | | 4350 | | | | | |

| Gly | Cys | Val | Lys | Asn | Leu | Val | Leu | His | Ser | Ala | Arg | Pro | Gly | Ala |
| | 4355 | | | | 4360 | | | | 4365 | | | | | |

| Pro | Pro | Pro | Gln | Pro | Leu | Asp | Leu | Gln | His | Arg | Ala | Gln | Ala | Gly |
| | 4370 | | | | 4375 | | | | 4380 | | | | | |

| Ala | Asn | Thr | Arg | Pro | Cys | Pro | Ser |
| | 4385 | | | | 4390 | | |

<210> SEQ ID NO 5
<211> LENGTH: 14327
<212> TYPE: DNA
<213> ORGANISM: Homo sapiens

<400> SEQUENCE: 5

```
ggccggcgag cgggcggctg cgggcggcgc ggagcgggcg gcgcggagcg agcgagcgag        60
agagcggcgc gggccgggcc atggggtggc gggcgccggg cgcgctgctg ctggcgctgc       120
tgctgcacgg gcggctgctg gcggtgaccc atgggctgag gcatacgat ggcttgtctc        180
tgcctgagga catagagacc gtcacagcaa gccaaatgcg ctggacacat tcgtaccttt       240
ctgatgatga gtacatgctg gctgacagca tctcaggaga cgacctgggc agtggggacc       300
tgggcagcgg ggacttccag atggtttatt ccgagccct ggtgaatttc actcgctcca       360
tcgagtacag ccctcagctg gaggatgcag gctccagaga gtttcgagag gtgtccgagg       420
ctgtggtaga cacgctggag tcggagtact tgaaaattcc cggagaccag ttgtcagtg        480
tggtgttcat caaggagctg gatggctggg tttttgtgga gctcgatgtg ggctcggaag       540
ggaatgcgga tggtgctcag attcaggaga tgctgctcag ggtcatctcc agcggctctg       600
tggcctccta cgtcacctct cccccaggat tccagttccg acgcctgggc acagtgcccc       660
agttcccaag agcctgcacg gaggccgagt ttgcctgcca cagctacaat gagtgtgtgg       720
ccctggagta tcgctgtgac cggcggcccg actgcaggga catgtctgat gagctcaatt       780
gtgaggagcc agtcctgggt atcagcccca cattctctct ccttgtggag acgacatctt       840
taccgccccg ccagagacaa ccatcatgc gacagccacc agtcacccac gctcctcagc        900
ccctgcttcc cggttccgtc aggcccctgc cctgtgggcc ccaggaggcc gcatgccgca       960
atgggcactg catccccaga gactacctct cgacggaca ggaggactgc gaggacggca      1020
gcgatgagct agactgtggc ccccccgccac cctgtgagcc caacgagttc ccctgcggga      1080
atggacattg tgccctcaag ctgtggcgct gcgatggtga ctttgactgt gaggaccgaa      1140
ctgatgaagc caactgcccc accaagcgtc tgaggaagt gtgcgggccc acacagttcc      1200
gatgcgtctc taccaacatg tgcatcccag ccagcttcca ctgtgacgag gagagcgact      1260
gtcctgaccg gagcgacgag tttgctgca tgcccccca ggtggtgaca cctcccggg        1320
agtccatcca ggcttcccgg ggccagacag tgaccttcac ctgcgtggcc attggcgtcc      1380
ccacccccat catcaattgg aggctcaact ggggccacat ccctctcat cccagggtga      1440
cagtgaccag cgagggtggc cgtggcacac tgatcatccg tgatgtgaag gagtcagacc      1500
agggtgccta cacctgtgag gccatgaacg ccgggggcat ggtgtttggc attcctgacg      1560
gtgtccttga gctcgtccca caacgaggcc cctgccctga cggccacttc tacctggagc      1620
```

```
acagcgccgc ctgcctgccc tgcttctgct ttggcatcac cagcgtgtgc cagagcaccc   1680
gccgcttccg ggaccagatc aggctgcgct ttgaccaacc cgatgacttc aagggtgtga   1740
atgtgacaat gcctgcgcag cccggcacgc caccctctc ctccacgcag ctgcagatcg    1800
acccatccct gcacgagttc cagctagtag acctgtcccg ccgcttcctc gtccacgact   1860
ccttctgggc tctgcctgaa cagttcctgg caacaaggt ggactcctat ggcggctccc    1920
tgcgttacaa cgtgcgctac gagttggccc gtggcatgct ggagccagtg cagcggccgg   1980
acgtggtcct cgtgggtgcc gggtaccgcc tcctctcccg aggccacaca cccacccaac   2040
ctggtgctct gaaccagcgc caggtccagt tctctgagga gcactgggtc catgagtctg   2100
gccggccggt gcagcgcgcg gagctgctgc aggtgctgca gagcctggag gccgtgctca   2160
tccagaccgt gtacaacacc aagatggcta gcgtgggact tagcgacatc gccatggata   2220
ccaccgtcac ccatgccacc agccatggcc gtgcccacag tgtggaggag tgcagatgcc   2280
ccattggcta ttctggcttg tcctgcgaga gctgtgatgc ccacttcact cgggtgcctg   2340
gtgggcccta cctgggcacc tgctctggtt gcagttgcaa tggccatgcc agctcctgtg   2400
accctgtgta tggccactgc ctgaattgcc agcacaacac ggaggggcca cagtgcaaca   2460
agtgcaaggc tggcttcttt ggggacgcca tgaaggccac ggccacttcc tgccggccct   2520
gcccttgccc atacatcgat gcctcccgca gattctcaga cacttgcttc ctggacacgg   2580
atggccaagc cacatgtgac gcctgtgccc caggctacac tggccgccgc tgtgagagct   2640
gtgccccgg atacgagggc aaccccatcc agcccggcgg gaagtgcagg cccgtcaacc   2700
aggagattgt gcgctgtgac gagcgtggca gcatggggac ctccggggag gcctgccgct   2760
gtaagaacaa tgtggtgggg cgcttgtgca atgaatgtgc tgacggctct ttccacctga   2820
gtacccgaaa ccccgatggc tgcctcaagt gcttctgcat gggtgtcagt cgccactgca   2880
ccagctcttc atggagccgt gcccagttgc atggggcctc tgaggagcct ggtcacttca   2940
gcctgaccaa cgccgcaagc acccacacca ccaacgaggg catcttctcc cccacgcccg   3000
gggaactggg attctcctcc ttccacagac tcttatctgg accctacttc tggagcctcc   3060
cttcacgctt cctgggggac aaggtgacct cctatggagg agagctgcgc ttcacagtga   3120
cccagaggtc ccagccgggc tccacacccc tgcacgggca gccgttggtg gtgctgcaag   3180
gtaacaacat catcctagag caccatgtgg cccaggagcc cagccccggc cagcccagca   3240
ccttcattgt gcctttccgg gagcaagcat ggcagcggcc cgatgggcag ccagccacac   3300
gggagcacct gctgatggca ctggcaggca tcgacaccct cctgatccga gcatcctacg   3360
cccagcagcc cgctgagagc agggtctctg catcagcat ggacgtggct gtgcccgagg   3420
aaaccggcca ggaccccgcg ctggaagtgg aacagtgctc ctgcccaccc gggtaccgtg   3480
ggccgtcctg ccaggactgt gacacaggct acacacgcac gcccagtggc ctctacctgg   3540
gtacctgtga acgctgcagc tgccatggcc actcagaggc ctgcgagcca gaaacaggtg   3600
cctgccaggg ctgccagcat cacacggagg ccctcggtg tgagcagtgc cagcaggat    3660
actacgggga cgcccagcgg gggacaccac aggactgcca gctgtgcccc tgctacggag   3720
accctgctgc cggccaggct gcccacactt gttttctgga cacagacggc cacccccacct   3780
gtgatgcgtg ctccccaggc cacagtgggc gtcactgtga gaggtgcgcc cctggctact   3840
atggcaaccc cagccagggc cagccatgcc agagagacag ccaggtgcca gggcccatag   3900
gctgcaactg tgaccccaa ggcagcgtca gcagccagtg tgatgctgct ggtcagtgcc    3960
```

```
agtgcaaggc ccaggtagaa ggcctcactt gcagccactg ccggcccac cacttccacc    4020 tgagtgccag caacccagac ggctgcctgc cctgcttctg tatgggcatc acccagcagt    4080
gcgccagctc tgcctacaca cgccacctga tctccaccca ctttgcccct ggggacttcc    4140
aaggctttgc cctggtgaac ccacagcgaa acagccgcct gacaggagaa ttcactgtgg    4200
aacccgtgcc cgagggtgcc cagctctctt ttggcaactt tgcccaactc ggccatgagt    4260
ccttctactg gcagctgccg gagacatacc agggagacaa ggtggcggcc tacggtggga    4320
agttgcgata caccctctcc tacacagcag gcccacaggg cagcccactc tcggaccccg    4380
atgtgcagat cacgggcaac aacatcatgc tagtggcctc ccagcagcg ctgcagggcc    4440 cagagaggag gagctacgag atcatgttcc gagaggaatt ctggcgccgg cccgatgggc    4500
agccggccac acgcgagcac ctcctgatgg cactggccga cctggatgag ctcctgatcc    4560
gggccacgtt ctcctccgtg ccgctggtgg ccagcatcag cgcagtcagc ctggaggtcg    4620
cccagccggg gccctcaaac agaccccgcg ccctcgaggt ggaggagtgc cgctgcccgc    4680
caggctacat cggtctgtcc tgccaggact gtgcccccgg ctacacgcgc accgggagtg    4740
ggctctacct cggccactgc gagctatgtg aatgcaatgg ccactcagac ctgtgccacc    4800
cagagactgg ggcctgctcg caatgccagc acaacgccgc aggggagttc tgcgagcttt    4860
gtgcccctgg ctactacgga gatgccacag ccgggacgcc tgaggactgc agccctgtg    4920 cctgcccact gaccaaccca gagaacatgt tttcccgcac ctgtgagagc tgggagccg    4980 gcgggtaccg ctgcacggcc tgcgaacccg gctacactgg ccagtactgt gagcagtgtg    5040
gcccaggtta cgtgggtaac cccagtgtgc aaggggggcca gtgcctgcca gagacaaacc    5100
aagccccact ggtggtcgag gtccatcctg ctcgaagcat agtgcccaa ggtggctccc    5160 actccctgcg gtgtcaggtc agtgggagcc cacccacta cttctattgg tcccgtgagg    5220
atgggcggcc tgtgcccagc ggcacccagc agcgacatca aggctccgag ctccacttcc    5280
ccagcgtcca gccctcggat gctgggggtct acatttgcac ctgccgtaat ctccaccaat    5340
ccaataccag ccgggcagag ctgctggtca ctgaggctcc aagcaagccc atcacagtga    5400
ctgtggagga gcagcggagc cagagcgtgc gccccggagc tgacgtcacc ttcatctgca    5460
cagccaaaag caagtcccca gcctataccc tggtgtggac ccgcctgcac aacgggaaac    5520
tgcccacccg agccatggat ttcaatggca tcctgaccat tcgcaacgtc cagctgagtg    5580
atgcaggcac ctacgtgtgc accggctcca acatgtttgc catggaccag ggcacagcca    5640
ctctacatgt gcaggcctcg ggcaccttgt ccgcccccgt ggtctccatc catccgccac    5700
agctcacagt gcagcccggg caactggcgg agttccgctg cagcgccaca gggagcccca    5760
cgcccaccct cgagtggaca gggggccccg gcggccagct ccctgcgaag gcacaaatcc    5820
acggcggcat cctgcgcctg ccagctgtcg agcccacgga tcaggcccag tacttgtgcc    5880
gagcccacag cagcgctggg cagcaggtgg ccagggctgt gctccacgtg catggggcg    5940 gtgggcccag agtccaagtg agcccagaga ggacccaggt ccacgcaggc cggaccgtca    6000
ggctgtactg cagggctgca ggcgtgccta gcgccaccat cacctggagg aaggaagggg    6060
gcagcctccc accacaggcc cggtcagagc gcacagacat cgcgacactg ctcatcccag    6120
ccatcacgac tgctgacgcc ggcttctacc tctgcgtggc caccagccct gcaggcactg    6180
cccaggcccg gatgcaagtg gttgtccttt cagcctcaga tgccagccca ccggggtca    6240 agattgagtc ctcatcgcct tctgtgacag aagggcaaac actcgacctc aactgtgtgg    6300
tggcagggtc agcccatgcc caggtcacct ggtacaggcg agggggtagc ctgcctcccc    6360
```

```
acacccaggt gcacggctcc cgtctgcggc tccccaggt ctcaccagct gattctggag    6420
aatatgtgtg ccgtgtggag aatggatcgg gccccaagga ggcctccatt actgtgtctg    6480
tgctccacgg cacccattct ggccccagct acacccagt gcccggcagc acccggccca    6540
tccgcatcga gccctcctcc tcacacgtgg cggaagggca gaccctggat ctgaactgcg    6600
tggtgcccgg gcaggccacc gcccaggtca cgtggcacaa gcgtggggc agcctccctg    6660 cccggcacca gacccacggc tcgctgctgc ggctgcacca ggtgaccccg gccgactcag    6720
gcgagtatgt gtgccatgtg gtgggcacct ccggccccct agaggcctca gtcctggtca    6780
ccatcgaagc ctctgtcatc cctggaccca tcccacctgt caggatcgag tcttcatcct    6840
ccacagtggc cgagggccag accctggatc tgagctgcgt ggtggcaggg caggcccacg    6900
cccaggtcac atggtacaag cgtgggggca gcctccctgc ccggcaccag gttcgtggct    6960
cccgcctgta catcttccag gcctcacctg ccgatgcggg acagtacgtc tgccgggcca    7020
gcaacggcat ggaggcctcc atcacggtca cagtaactgg gacccagggg gccaacttag    7080
cctaccctgc cggcagcacc cagcccatcg catcgagcc ctcctcctcg caagtggcgg    7140
aagggcagac cctggatctg aactgcgtgg tgcccgggca gtcccatgcc caggtcacgt    7200
ggcacaagcg tgggggcagc ctccctgtcc ggcaccagac ccacggctcc ctgctgagac    7260
tctaccaagc gtcccccgcc gactcgggcg agtacgtgtg ccgagtgttg ggcagctccg    7320
tgcctctaga ggcctctgtc ctggtcacca ttgagcctgc gggctcagtg cctgcacttg    7380
gggtcacccc cacggtccgg atcgagtcat cgtcttcgca agtggccgag gggcagaccc    7440
tggacctgaa ctgcctcgtt gctggtcagg cccatgccca ggtcacgtgg cacaagcgcg    7500
ggggcagcct cccggcccgg caccaggtgc atggctcgag gctacgcctg ctccaggtga    7560
ccccagctga ttcaggggag tacgtgtgcc gtgtggtcgg cagctcaggt acccaggaag    7620
cctcagtcct tgtcaccatc cagcagcgcc ttagtggctc ccactcccag ggtgtggcgt    7680
accccgtccg catcgagtcc tcctcagcct ccctggccaa tggacacacc ctggacctca    7740
actgcctggt tgccagccag gctccccaca ccatcacctg gtataagcgt ggaggcagct    7800
tacccagccg gcaccagatc gtgggctccc ggctgcggat ccctcaggtg actccggcag    7860
actcgggcga gtacgtgtgt cacgtcagta acggtgcagg ctcccgggag acctcgctca    7920
tcgtcaccat ccagggcagc ggttcctccc acgtgcccag cgtctcccca ccgatcagga    7980
tcgagtcgtc ttcccccacg gtggtggaag ggcagacctt ggatctgaac tgcgtggtcg    8040 ccagcagcc ccaggctatc atcacatggt acaagcgtgg gggcagcctt ccctcccgac    8100
accagaccca tggctcccac ctgcggttgc accaaatgtc tgtggctgac tcgggcgagt    8160
atgtgtgccg ggccaacaac aacatcgatg ccctggaggc ctccatcgtc atctccgtct    8220 ccctagcgc cggcagcccc tccgcccctg gcagctccat gcccatcaga attgagtcat    8280
cctcctcaca cgtggccgaa ggggagaccc tggatctgaa ctgcgtggtc cccgggcagg    8340
cccatgccca ggtcacttgg cacaagcgtg ggggcagcct ccccagtcac catcagaccc    8400
gcggctcacg gctgcggctg caccatgtgt ccccggccga ctcgggtgaa tacgtgtgcc    8460
gggtgatggg cagctctggc ccctggagg cctcagtcct ggtcaccatc gaagcctctg    8520
gctcaagtgc tgtccacgtc cccgcccag gtggagcccc acccatccgc atcgagccct    8580
cctcctcccg agtggcagaa gggcagaccc tggatctgaa gtgcgtggtg cccgggcagg    8640
cccacgccca ggtcacatgg cacaagcgtg aggaaacct ccctgccggg caccaggtcc    8700
```

| | |
|---|---|
| acggcccact gctgaggctg aaccaggtgt ccccggctga ctctggcgag tactcgtgcc | 8760 |
| aagtgaccgg aagctcaggc accctggagg catctgtcct ggtcacaatt gagccctcca | 8820 |
| gcccaggacc cattcctgct ccaggactgg cccagcccat ctacatcgag gcctcctctt | 8880 |
| cacacgtgac tgaagggcag actctggatc tgaactgtgt ggtgcccggg caggcccatg | 8940 |
| cccaggtcac gtggtacaag cgcggggca gcctccccgc ccggcaccag acccatggct | 9000 |
| cccagctgcg gctccacctc gtctccctg ccgactcagg cgagtatgtg tgtcgtgcag | 9060 |
| ccagcggccc aggccctgag caagaagcct ccttcacagt caccgtcccg cccagtgagg | 9120 |
| ggtcttccta ccgccttagg agcccggtca tctccatcga cccgcccagc agcaccgtgc | 9180 |
| agcagggcca ggatgccagc ttcaagtgcc tcatccatga cggggcagcc cccatcagcc | 9240 |
| tcgagtggaa gacccggaac caggagctgg aggacaacgt ccacatcagt cccaatggct | 9300 |
| ccatcatcac catcgtgggc acccggccca gcaaccacgg tacctaccgc tgcgtggcct | 9360 |
| ccaatgccta cggtgtggcc cagagtgtgg tgaacctcag tgtgcacggg cccctacag | 9420 |
| tgtccgtgct ccccgagggc cccgtgtggg tgaaagtggg aaaggctgtc accctggagt | 9480 |
| gtgtcagtgc cggggagccc cgctcctctg ctcgttggac ccggatcagc agcaccctg | 9540 |
| ccaagttgga gcagcggaca tatgggctca tggacagcca cgcggtgctg cagatttcat | 9600 |
| cagctaaacc atcagatgcg ggcacttatg tgtgccttgc tcagaatgca ctaggcacag | 9660 |
| cacagaagca ggtggaggtg atcgtggaca cgggcgccat ggccccaggg gcccctcagg | 9720 |
| tccaagctga agaagctgag ctgactgtgg aggctggaca cacggccacc ttgcgctgct | 9780 |
| cagccacagg cagccccgcg cccaccatcc actggtccaa gctgcgttcc ccactgccct | 9840 |
| ggcagcaccg gctggaaggt gacacactca tcatacccc ggtagcccag caggactcgg | 9900 |
| gccagtacat ctgcaatgcc actagccctg ctgggcacgc tgaggccacc atcatcctgc | 9960 |
| acgtggagag cccaccatat gccaccacg tcccagagca cgcttcggtg caggcagggg | 10020 |
| agacggtgca gctccagtgc ctggctcacg ggacaccccc actcaccttc cagtggagcc | 10080 |
| gcgtgggcag cagccttcct gggagggcga ccgccaggaa cgagctgctg cactttgagc | 10140 |
| gtgcagcccc tgaggactca ggccgctacc gctgccgggt caccaacaag gtgggctcag | 10200 |
| ccgaggcctt tgcccagctg ctcgtccaag ccctcccgg ctctctccct gccacctcca | 10260 |
| tcccagcagg gtccacgccc accgtgcagg tcacgcctca gctagagacc aagagcattg | 10320 |
| gggccagcgt tgagttccac tgtgctgtgc ccagcgacca gggtacccag ctccgttggt | 10380 |
| tcaaggaagg gggtcagctg cctccgggtc acagcgtgca ggatgggtg ctccgaatcc | 10440 |
| agaacttgga ccagagctgc caagggacgt atatatgcca ggcccatgga ccttggggga | 10500 |
| aggcccaggc cagtgcccag ctggttatcc aagccctgcc ctcggtgctc atcaacatcc | 10560 |
| ggacctctgt gcagaccgtg gtggttggcc acgccgtgga gttcgaatgc ctggcactgg | 10620 |
| gtgaccccaa gctcaggtg acatggagca agttggagg gcacctgcgg ccaggcattg | 10680 |
| tgcagagcgg aggtgtcgtc aggatcgccc acgtagagct ggctgatgcg ggacagtatc | 10740 |
| gctgcactgc caccaacgca gctggcacca cacaatccca cgtcctgctg cttgtgcaag | 10800 |
| ccttgcccca gatctcaatg ccccaagaag tccgtgtgcc tgctggttct gcagctgtct | 10860 |
| tcccctgcat agcctcaggc tacccccactc ctgacatcag ctggagcaag ctggatgcca | 10920 |
| gcctgccacc tgacagccgc ctggagaaca catgctgat gctgccctca gtccgacccc | 10980 |
| aggacgcagg tacctacgtc tgcaccgcca ctaaccgcca gggcaaggtc aaagccttg | 11040 |
| cccacctgca ggtgccagag cgggtggtgc cctacttcac gcagacccc tactccttcc | 11100 |

```
taccgctgcc caccatcaag gatgcctaca ggaagttcga gatcaagatc accttccggc   11160
ccgactcagc cgatgggatg ctgctgtaca atgggcagaa gcgagtccca gggagcccca   11220
ccaacctggc caaccggcag cccgacttca tctccttcgg cctcgtgggg ggaaggcccg   11280
agttccggtt cgatgcaggc tcaggcatgg ccaccatccg ccatcccaca ccactggccc   11340
tgggccattt ccacaccgtg accctgctgc gcagcctcac ccaggctcc ctgattgtgg   11400
gtgacctggc cccggtcaat gggacctccc agggcaagtt ccagggcctg atctgaacg   11460
aggaactcta cctgggtggc tatcctgact atggtgccat ccccaaggcg gggctgagca   11520
gcggcttcat aggctgtgtc cgggagctgc gcatccaggg cgaggagatc gtcttccatg   11580
acctcaacct cacggcgcac ggcatctccc actgccccac ctgtcgggac cggcctgcc    11640
agaatggcgg tcagtgccat gactctgaga gcagcagcta cgtgtgcgtc tgcccagctg   11700
gcttcaccgg gagccgctgt gagcactcgc aggccctgca ctgccatcca gaggcctgtg   11760
ggcccgacgc cacctgtgtg aaccggcctg acggtcgagg ctacacctgc cgctgccacc   11820
tgggccgctc ggggttgcgg tgtgaggaag gtgtgacagt gaccacccc tcgctgtcgg    11880
gtgctggctc ctacctggca ctgcccgccc tcaccaacac acaccacgag ctacgcctgg   11940
acgtggagtt caagccactc gcccctgacg gggtcctgct gttcagcggg gggaagagcg   12000
ggcctgtgga ggacttcgtg tccctggcga tggtgggcgg ccacctggag ttccgctatg   12060
agttggggtc agggctggcc gttctgcgga gcgccgagcc gctggccctg ggccgctggc   12120
accgtgtgtc tgcagagcgt ctcaacaagg acggcagcct gcgggtgaat ggtggacgcc   12180
ctgtgctgcg ctcctcgccc ggcaagagcc agggcctcaa cctgcacacc ctgctctacc   12240
tgggggggtgt ggagccttcc gtgccactgt ccccggccac caacatgagc gctcacttcc   12300
gcggctgtgt gggcgaggtg tcagtgaatg gcaaacggct ggacctcacc tacagtttcc   12360
taggcagcca gggcatcggg caatgctatg atagctcccc atgtgagcgc cagccttgcc   12420
aacatggtgc cacgtgcatg cccgctggcg agtatgagtt ccagtgcctg tgtcgagatg   12480
gattcaaagg agacctgtgt gagcacgagg agaaccctg ccagctccgt gaaccctgtc    12540
tgcatggggg cacctgccag ggcacccgct gcctctgcct ccctggcttc tctggcccac   12600
gctgccaaca ggctctggga catggcatag cagagtccga ctggcatctt gaaggcagcg   12660
ggggcaatga tgcccctggg cagtacggag cctatttcca cgatgatggc ttcctcgcct   12720
tccctggcca tgtcttctcc aggagcctgc ccgaggtgcc cgagaccatc gagctggagg   12780
ttcggaccag cacagccagt ggcctcctgc tctggcaggg tgtggaggtg ggagaggccg   12840
gccaaggcaa ggacttcatc agcctcgggc ttcaagacgg gcaccttgtc ttcaggtacc   12900
agctgggtag tggggaggcc cgcctggtct ctgaggaccc catcaatgac ggcgagtggc   12960
accgggtgac agcactgcgg gagggccgca gaggttccat ccaagtcgac ggtgaggagc   13020
tggtcagcgg ccggtcccca ggtcccaacg tggcagtcaa cgccaagggc agcgtctaca   13080
tcggcggagc ccctgacgtg gccacgctga ccggggcag attctcctcg gcatcacag    13140
gctgtgtcaa gaacctggtg ctgcactcgg cccgaccgg cgccccgccc ccacagcccc    13200
tggacctgca gcaccgcgcc caggccgggg ccaacacacg ccctgccc tcgtaggcac     13260
ctgcctgccc cacacggact cccggccac gccccagccc gacaatgtcg agtatattat    13320
tattaatatt attatgaatt tttgtaagaa accgaggcga tgccacgctt tgctgctacc   13380
gccctgggct ggactggagg tgggcatgcc accctcacac acacagctgg gcaaagccac   13440
```

```
aaggctggcc agcaaggcag gttggatggg agtgggcacc tcagaaagtc accaggactt  13500
ggggtcagga acagtggctg ggtgggccca gaactgcccc cactgtcccc ctacccaccg  13560
atggagcccc cagatagagc tgggtggcct gtttctgcag cccttgggca gttctcactc  13620
ctaggagagc caacctcggc ttgtgggctg gtgcccaca gctacctgag acgggcatcg   13680
caggagtctc tgccacccac tcaggattgg gaattgtctt tagtgccggc tgtggagcaa  13740
aaggcagctc acccctgggc aggcggtccc catcccacc agctcgtttt tcagcacccc   13800
cacccacctc cacccagccc ctggcacctc ctctggcaga ctcccctcc taccacgtcc    13860 tcctggcctg cattcccacc ccctcctgcc agcacacagc ctggggtccc tccctcaggg  13920
gctgtaaggg aaggcccacc ccaactctta ccaggagctg ctacaggcag agcccagcac  13980
tgatagggcc ccgcccaccg ggccccgccc accccaggcc acatccccac ccatctggaa  14040
gtgaaggccc agggactcct ccaacagaca acggacggac ggatgccgct ggtgctcagg  14100
aagagctagt gccttaggtg ggggaaggca ggactcacga ctgagagaga gaggaggggg  14160
atatgaccac cctgccccat ctgcaggagc ctgaagatcc agctcaagtg ccatcctgcc  14220
agtggccccc agactgtggg gttgggacgc ctggcctctg tgtcctagaa gggaccctcc  14280
tgtggtcttt gtcttgattt ttcttaataa acggtgctat ccccgcc              14327
```

WOUND AND CUTANEOUS INJURY HEALING WITH A NUCLEIC ACID ENCODING PERLECAN

CROSS-REFERENCE TO RELATED APPLICATIONS

The present disclosure is a continuation of U.S. patent application Ser. No. 10/420,270, filed Apr. 22, 2003, now U.S. Pat. No. 7,141,551, issued Nov. 28, 2006, which claims priority to and benefit of U.S. Provisional Patent Application No. 60/374,553, filed Apr. 22, 2002.

FIELD OF DISCLOSURE

The present disclosure relates to biomolecules involved in wound healing and angiogenesis.

BACKGROUND

Perlecan, originally named heparan sulfate proteoglycan, is now known to be an important component of all basement membranes (along with collagen type IV and laminin) and is thought to play a role in wound healing and angiogenesis. Perlecan consists of three heparan sulfate side chains linked to a large core protein of approximately 450 kDa (32, 36). This sequence has a single open reading frame of at least 3,707 amino acids that encodes for a protein of 396-466 kDa. Sequence analysis of the deduced sequences show the protein consists of five different domains, most of which contain internal repeats. Domain I contains a start methionine followed by a typical signal transfer sequence and a unique segment of 172 amino acids that contains the three probable sites of heparan sulfate attachment (of the amino acid sequence SGD). Domain II contains four strictly conserved cysteine-rich and acidic amino acid repeats that are very similar to those found in the LDL receptor and proteins such as megalin/GP330. Domain III consists of cysteine-rich and globular regions, both of which show similarity to those in the short arm of the laminin A chain. Domain IV contains 14 repeats of the immunoglobulin superfamily that are most highly similar to the immunoglobulin-like repeats in the neural cell adhesion molecule, and it appears domain IV has the capacity for differential splicing. Recombinant domain IV of perlecan binds to nidogens, laminin-nidogen complex, fibronectin, fibulin-2 and heparin (24). Domain V is the COOH-terminal domain and contains three repeats with similarity to the laminin A chain G domain. The repeats are separated by epidermal growth factor-like regions not found in the laminin A chain. Perlecan domain V is considered important in the supramolecular assembly of, and cell connections to, basement membranes (5).

The primary structural data agree with the appearance of the molecule in the electron microscope as a series of globules separated by rods, or "beads on a string." Therefore, the name perlecan was adopted for this molecule (36). In summary, the variety of domains in perlecan suggests multiple interactions with other molecules, and each domain of native perlecan has the potential for separate functional activities related to wound healing and/or angiogenesis.

Expression of Perlecan

Native perlecan has been purified from the mouse Englebroth Holm Swarm (EHS) tumor (22), porcine kidneys (16), bovine kidneys (21), from the conditioned medium of bovine aortic endothelial cells (39), and from the extracellular matrix of cultured human fetal lung fibroblasts (2). Other sources of perlecan may also be available and the above list is not meant to be inclusive. The individual domains of perlecan have also been individually expressed in native configuration from bacterial hosts (33) and eukaryotic hosts (8, 10, 20). The obvious domain structure and limited susceptibility to proteolysis (11) contribute to the ability to produce each of the perlecan domains individually. For example, domain 1 has been cloned and expressed alone (10, 19), and with portions of domain II (20). It is known that sequences in the protein core affect the amount and type of glycosaminoglycan (such as heparan sulfate) which is attached when perlecan is produced in a eukaryotic host. However, the biological significance of the different glycosylation patterns remains unknown.

In situ hybridization studies and immunoenzymatic studies show a close association of perlecan with a variety of cells involved in the assembly of basement membranes, in addition to being localized within the stromal elements of various connective tissues. Perlecan has been demonstrated in periodontal ligament fibroblasts (29). Perlecan has also been detected in the basement membranes of human tissues including pituitary gland, skin, breast, thymus, prostate, colon, liver, pancreas, spleen, heart, and lung. All vascular basement membranes reported to be tested contained perlecan. In addition, sinusoidal vessels of liver, spleen, lymph nodes, and pituitary gland expressed high levels of perlecan in the sub-endothelial region. In situ hybridization, using as probe human cDNA-encoding Domain III, localized perlecan mRNA to specific cell types within the tissues and demonstrated that in skin, perlecan appears to be synthesized exclusively by connective tissue cells in the dermal layer (32, 33). Perlecan is also highly expressed in human bone marrow (28) and in synovium (13). An immunohistochemical study confirmed the location of perlecan on the apical cell surface of endothelial cells, and additionally as a dense fibrillar network surrounding the cells. In this context, the binding of thrombospondin 1 to the apical surface of endothelial cells, which is critical in angiogenesis (44), was found to be dependent upon the $NH_2$-terminal heparan sulfate chains of perlecan (45). These patterns of perlecan expression clearly implicate a role in wound healing regulation and/or angiogenesis.

Cell and Growth Factor Binding

Perlecan is adhesive for fibroblasts and endothelial cells (28). Expression of perlecan in the mouse was coordinated with development of attachment competence by mouse embryos in vitro and in utero (7). Purified perlecan and laminin were found to promote attachment of immortalized rat chondrocytes in vitro (43). Perlecan is thought to modulate binding between the basement membrane structure and various cells, including smooth muscle cells and aortic endothelial cells, through a non-RGD cell binding region in one of the perlecan domains (possibly domain III in the mouse; amino acid sequence LPASFRGDKVTSY (SEQ ID NO: 1), as well as by GRGDSP (SEQ ID NO: 2), but not GRGESP (SEQ ID NO: 3)) and integrins β-1 and α-5, β-3 (23). Alternatively, other investigators have found that the attachment of Rugli cells (a rat glioma derived cell line), mesenchymal, and epithelial derived tumor cell lines to mouse perlecan did not involve the protein core and was totally dependent on the presence of the heparan sulfate, although binding through the β-1 integrin of the cells was involved (4). Cell adhesion to perlecan was low compared to perlecan core alone (23). Human endothelial cell-derived perlecan was shown to bind endothelial cells in vitro with contributions from the heparan sulfate and from the protein core (46). The attachment of cells to the protein core of human perlecan further supports the implication of alternative cell binding pathways as the human homologue does not have the RGD sequence in domain III. Significant evidence for a role in cell binding further implicates perlecan in wound healing processes.

Proteoglycans such as perlecan, once thought to primarily serve as structural components of extracellular matrix, are now being focused on for their role in tissue and cell regulation, particularly angiogenesis and wound healing. Many growth factors, notably the fibroblast growth factor family (FGF) which now numbers 19 members, bind to heparin and heparan sulfate proteoglycans, and this binding has been shown to have a significant impact on the availability and activity of these growth factors. Importantly, perlecan has been shown to specifically bind to FGF-2 (also known as bFGF), which is critical in vascular development and wound healing (37). Perlecan was found to induce high affinity binding of FGF-2 both to cells deficient in heparan sulfate and to soluble FGF receptors. Further, in a rabbit ear model for in vivo angiogenesis, perlecan was a potent inducer of FGF-2-mediated neovascularization (2). It has been shown that FGF-2 binds to the heparin sulfate on domain I of perlecan (2) and that FGF-2 is released by biologically relevant enzymes such as plasmin, collagenase, and heparinases, which may have a role in the regulation of the growth factor activity (47). Mitogenic keratinocyte growth factor (FGF-7) was recently shown to bind to domains III and V of the perlecan protein core (31). Binding of FGF-2 to the heparan sulfate chain of perlecan is thought to involve three-way coordinated binding between FGF, heparan sulfate, and the FGF receptor, and to involve specific sites of sulfation (unpublished data). The FGF receptor is probably the FGF-binding protein that was recently reported to bind perlecan specifically in domain III (30).

Perlecan is also able to bind the growth factor granulocyte/macrophage-colony stimulating factor and present it to hematopoietic progenitor cells in a semi-solid colony assay (28). Bound growth factors can be released by enzymes, which are present during wound healing, such as the matrix metalloproteinases (47). Ligand binding itself can lead to internalization through a perlecan-mediated process, as has been shown for ligands such as lipoproteins (15). Binding of growth factors is clearly an important role of perlecan in wound healing and angiogenesis.

Breached basement membranes in vascular, corneal, and dermal tissues must respond quickly to the injury with repair. Such a rapid response suggests storage of needed biomolecules to effect repairs and remodeling. Cells involved in the wound healing and angiogenic process may have a ready and ample storage of FGF and other growth factors bound to perlecan in the basement membrane adjoining the wound. It has been demonstrated that enzymes which are turned on in the remodeling wound and angiogenesis, such as the matrix metalloproteinases (MMPs), stromelysin, rat collagenase, plasmin, urokinase, heparitinase I, and heparin, may modulate the bioavailability of the growth factors by degrading the protein core and removing the glycosaminoglycans (47). The MMPs are required in correct wound healing and in angiogenesis, and have been shown to bind to cells. The extracellular binding of MMPs could position the enzyme for directed proteolytic attack, for activation of other MMPs, and for regulation of other cell surface proteins. It has recently been demonstrated that heparin binds (5-10 nM) MMP-7, MMP-2, MMP-9, and MMP-13. This suggests that the MMPs may be positioned on the cell surface or retained in the ECM by perlecan heparan sulfate chains (48).

Growth and Wound Healing

The effectiveness of perlecan as an exogenously added promoter of growth and neovascularization was demonstrated with anti-sense perlecan knockouts in colon carcinoma cells (40). Growth of colon carcinoma cells was markedly attenuated upon obliteration of perlecan gene expression and these effects correlated with reduced responsiveness to, and affinity for, FGF-7. Exogenous perlecan effectively reconstituted the activity of FGF-7 in the perlecan-deficient cells. Moreover, soluble FGF-7 specifically bound immobilized perlecan in a heparan sulfate-independent manner. In both tumor xenografts induced by human colon carcinoma cells and tumor allografts induced by highly invasive mouse melanoma cells, perlecan suppression caused substantial inhibition of tumor growth and neovascularization. Thus, perlecan is a potent inducer of cell growth and angiogenesis in vivo and therapeutic interventions targeting this key modulator of tumor progression may improve wound healing.

In cells that were expressing antisense perlecan, responses to increasing concentrations of FGF-2 were dramatically reduced in comparison to wild-type or vector-transfected cells as measured by thymidine incorporation and rate of proliferation (3). Furthermore, receptor binding and affinity labeling of cells expressing antisense perlecan indicated that eliminating perlecan expression (by expressing antisense perlecan) results in reduced high-affinity FGF-2 binding. Both the binding and mitogenic response of cells expressing antisense perlecan to FGF-2 could be rescued by exogenous perlecan (3).

Poor wound healing in diabetics and in diabetes-related periodontitis may be related to perlecan expression. High levels of glucose can decrease perlecan expression in some cells, probably through transcriptional and post-transcriptional mechanism (27). Further, it has recently been demonstrated that FGF-2 bound to perlecan is protected from inactivation by non-enzymatic glycation, which occurs during the course of diabetes (35). The relationship between poor expression and protection from inactivation in diabetes has not been investigated.

Evidence indicates that in cases of poor surgical wound closure and healing by frank secondary intention, as results in many barrier membrane surgeries during oral and periodontal surgeries, for example, the presence of perlecan in the subepithelial matrix is associated with healing of the wound up to 14 days post surgery, at which time the healed wound can appear normal in terms of perlecan core protein. Subsequently, sulfation levels of the heparan sulfate chains increase over the ensuing year of healing (1). Another investigation, however, reported that perlecan is not detectable under epithelial cells migrating over connective tissue and only appears when the wound is covered and a new basement membrane is deposited (38). In wounds that are remodeling over a period of weeks, perlecan levels in the subepithelial connective tissues appear to remain relatively high (42). The functional significance of various perlecan expression patterns during healing is not yet known, but it is clear the biomolecule has an important and fundamental role in the healing process.

In summary, a complex interplay exists between 1) extracellular matrix proteins, including perlecan, 2) the cells considered key in establishing dermal integrity such as fibroblasts, endothelial cells, epithelial cells, and 3) growth factors such as the FGF's. It is clear, however, that perlecan has the potential to affect several aspects of wound healing and, to that end, is an excellent candidate for application or induction in various forms, with or without the addition of various growth factors to modulate wound healing.

SUMMARY

The present disclosure describes the use of perlecan as an adjunct for the improvement of wound healing and/or angiogenesis. The disclosure describes the application of perlecan at an effective concentration in a pharmaceutically acceptable carrier, such as a paste, for use in a variety of processes. For example, perlecan may be used during periodontal procedures, such as flap surgery, or may be applied to sites of cutaneous injury such as burns and cuts, or may be applied to sites of surgical procedures, such as incisions, implants or grafts. Perlecan may be applied directly in a pharmaceutically acceptable carrier, or may be applied to a wound bandage or dressing, or may be absorbed to surgical implants, grafting materials or surgical barrier membranes. Perlecan may also be applied by delivery of nucleic acid encoding for perlecan. Perlecan nucleic acid may be delivered via viral vectors, cells expressing perlecan molecules, via naked nucleic acid (such as mRNA) or via liposome technology The present disclosure also encompasses the application of perlecan in conjunction with growth factors, such as FGF-2 or FGF-7, or other heparan sulfate binding growth factors. Evidence suggests that perlecan or its derivatives has the potential to effect the interplay between cells of the dermis and epidermis, the extracellular matrix, and various growth factors, each of which has a role in wound healing and or angiogenesis. Therefore, perlecan is an excellent candidate for application or delivery in various forms, possibly in conjunction with various growth factors, to modulate wound healing and/or angiogenesis.

DETAILED DESCRIPTION

In the present disclosure, the use of perlecan as an adjunct to wound healing and angiogenesis is described. As used in this specification and claims, the term "perlecan" refers to the polypeptide listed in SwissProt Protein Data Base named Heparan Sulfate Proteoglycan (accession number CAC18534.1) (SEQ ID NO: 4) or the nucleic acid coding sequence named Human Heparan Sulfate Proteoglycan (HSPG2) mRNA (GenBank accession number M85289.1) (SEQ ID NO: 5). In addition to the perlecan nucleic acid sequences disclosed in SEQ ID NO: 5, the present disclosure also is directed to nucleic acid sequences encoding functional derivatives of the perlecan nucleic acid. As used herein, a "functional derivative" includes the "fragments," "degenerate variation," "mutants," "analogs," "variants" and "chemical derivatives". The term "fragment" is meant to refer to any nucleic acid subset of the perlecan nucleic acid comprising at least 9 contiguous nucleic acid residues. The term "variant" is meant to refer to a molecule substantially similar in structure to either the entire perlecan gene, or to a fragment thereof. The term "chemical derivative" describes a nucleic acid or protein that contains additional chemical moieties which are not normally a part of the base molecule. Such moieties may alter the solubility, binding characteristics (to molecules such as growth factors) half-life, absorption, etc. of the base molecule. Alternatively the moieties may attenuate undesirable side effects of the base molecule or decrease the toxicity of the base molecule. Examples of such moieties are described in a variety of texts, such as *Remington The Science and Practice of Pharmacy*, 20$^{th}$ edition.

It is known that there is a substantial amount of redundancy in the codons which code for specific amino acids. Therefore, this disclosure is directed to those nucleic acid sequences which contain alternative codons which code for the eventual translation of the identical amino acid in SEQ. ID NO. 4. For purposes of this specification, a nucleic acid sequence coding for one or more alternative codons will be defined as a "degenerate variation." Also included within the scope of this disclosure are mutations either in the perlecan nucleic acid sequence which do not substantially alter the ultimate physical properties of the polypeptide encoded by the perlecan nucleic acid, or functional derivatives thereof (referred to as an "analog"). For example, an analog may comprise a conservative amino acid changes, such as, but not limited to, substitution of valine for leucine or asparagine for glutamine. Other examples of conservative amino acid changes may be found in Biochemistry, 2cd Edition Geoffrey Zubay (Macmilliam Publishing Company, New York, N.Y., Table 1-1, p 33) and include substitutions of an amino acids with other amino acid listed within the same grouping. It is known that DNA sequences coding for a polypeptide may be altered so as to code for a peptide having properties that are different than those of the naturally-occurring peptide (referred to as "mutants"). Mutant nucleic acid sequences may be isolated from nature. Methods of producing mutant nucleic acid sequences include, but are not limited to site directed mutagenesis. Examples of altered properties include, but are not limited to changes in the affinity of an enzyme for a substrate or a receptor for a ligand (such as but not limited to growth factors) and altered sulfation patterns. A molecule is "substantially similar" to the perlecan nucleic acid if both molecules have substantially similar structures, or if both molecules possess similar biological activity.

The disclosure also directed to polypeptides encoded by perlecan nucleic acid, or functional derivatives thereof. Therefore, the disclosure covers polypeptides coded for by fragments of the perlecan nucleic acid. In addition, the disclosure covers polypeptides coded for by analogs, degenerate variants and mutants of the perlecan nucleic acid.

A molecule is "substantially similar" to perlecan in terms of structure if both molecules have more than 50% similarity or 70% identity between their respective nucleotide or amino acid sequences. Forms of perlecan that varied in glycosaminoglycan profiles and sulfation patterns, including those forms of perlecan totally without glycosaminoglycan or sulfated constituents, would be considered molecules substantially similar to perlecan. As used in this disclosure, the term "percent homology" of two amino acid sequences or of two nucleic acid sequences is determined using the algorithm of Karlin and Altschul (Proc. Natl. Acad. Sci. USA 87: 2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). Blast nucleotide searches are performed with the NBLAST program, score=100, wordlength=12, to obtain nucleotide sequences homologous to a nucleic acid molecule of the invention. Blast protein searches are performed with the XBLAST program, score=50, wordlength=3 to obtain amino acid sequences homologous to a referenced polypeptide. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (XBLAST and NBLAST) are used.

Perlecan may be derived from purification from either natural or recombinant sources, standard cloning procedures, from proteolysis of cloned or native molecules, or by induction within host cells, or by delivery from cells expressing perlecan nucleic acid sequences. For example, a derivative of perlecan would include a recombinant perlecan protein expressed from a host cell where the fragment comprised both domains I and III of the native perlecan molecule, and where the nucleic acid coding for the recombinant perlecan molecule was mutated to alter the sulfation pattern when compared to native perlecan. In addition, perlecan may be used either alone or in the presence of a modulating compound (defined as a protein, nucleic acid or organic compound that modulates the structure and/or function and/or activity of perlecan). Examples of modulating compounds are growth factors, especially those growth factors of the fibroblast growth factor family, such as FGF-2 and FGF-7, and other growth factors that interact with the heparan sulfate chains.

As used in this disclosure, an isolated nucleic acid is a nucleic acid the structure of which is not identical to that of any naturally occurring nucleic acid, or to that of any fragment of a naturally occurring genomic nucleic acid spanning more than three separate genes. The term therefore covers, by way of example only, 1) a DNA which has the sequence of part of a naturally occurring genomic DNA molecule, but is not flanked by both of the sequences that flank that part of the molecule in the genome of the organism in which it naturally occurs; 2) a nucleic acid incorporated into a vector or into the genomic DNA of a prokaryote or eukaryote in a manner such that the resulting molecule is not identical to any naturally occurring genomic DNA; 3) a separate molecule such as a cDNA, a genomic fragment, a fragment produced by PCR, or a restriction fragment; and 4) a recombinant nucleotide sequence that is part of a hybrid gene (i.e., a gene encoding a fusion protein). Specifically excluded from this definition are nucleic acids present in mixtures of DNA molecules, transfected cells and cell clones, as these occur in a DNA library such as a cDNA or genomic library.

Perlecan may be recombinantly expressed either alone or in combination with a modulating compound by molecular cloning into an expression vector containing a suitable promoter and other appropriate transcription regulatory elements, and transferred into prokaryotic or eukaryotic host cells to produce recombinant molecules. Techniques for such manipulations are within the ordinary skill of one in the art, and representative techniques can be found described in Sambrook, J., et al., *Molecular Cloning* Second Edition, 1990, Cold Spring Harbor Press. Expression vectors are defined herein as the nucleic acid sequences that are required for the transcription of cloned copies of genes and the translation of their mRNAs in an appropriate host. Such vectors can be used to express eukaryotic genes in a variety of hosts such as bacteria, blue green algae, plant cells, insect cells, fungal cells and animal cells.

An appropriately constructed expression vector should contain, at the minimum: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. Expression vectors may include, but are not limited to, cloning vectors, modified cloning vectors, specifically designed plasmids or viruses.

A variety of expression vectors may be used for the expression of perlecan. These include, but are not limited to commercially available mammalian expression vectors such as pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Commercially available bacterial expression vectors that may be suitable for recombinant expression of perlecan include, but are not limited to, pET11a (Novagen), lambda gt11 (Invitrogen), pcDNAII (Invitrogen), pKK223-3 (Pharmacia). Commercially available insect cell expression vectors that may be suitable for recombinant expression of perlecan include, but are not limited to, pBlue Bac III (Invitrogen). The expression vectors may also be produced according to specific needs. The choice of the appropriate expression vector is within the ordinary skill of one in the art. The expression vector may contain nucleic acid coding only for the perlecan, or may encode for the perlecan, either alone or in combination with a modulating compound.

Recombinant host cells may be prokaryotic or eukaryotic, including but not limited to bacteria such as *E. coli*, fungal cells such as yeast, and mammalian cells, including, but not limited to, cell lines of human, bovine, porcine, monkey and rodent origin, and insect cells including, but not limited to, *Drosophila* and silkworm derived cell lines. A variety of cell lines derived from mammalian species which may be suitable for use as host cells are commercially available and include, but are not limited to, L cells L-M(TK.sup.-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). The choice of host cells is within the ordinary skill of one in the art.

The expression vectors may be introduced into host cells via any one of a number of techniques including but not limited to transformation, transfection, lipofection, protoplast fusion, and electroporation. The expression vector-containing cells are clonally propagated and individually analyzed to determine whether they produce the compound of interest. Identification of cells expressing the perlecan product, can be accomplished by a variety of means, including but not limited to, immunological reactivity, or the presence of host cell-associated perlecan activity.

Expression of perlecan, either alone or in combination with a modulating compound, may also be performed using in vitro produced synthetic mRNA or isolated native mRNA. Synthetic mRNA or mRNA isolated from perlecan producing cells can be efficiently translated in various cell-free systems, including but not limited to wheat germ extracts and reticulocyte extracts, as well as efficiently translated in cell based systems, including but not limited to microinjection into frog oocytes.

Following expression of perlecan in a recombinant host cell, which host cell may also be expressing a modulating compound, purified perlecan, or purified perlecan in association with a modulating compound may be obtained. Purification methods for isolating expressed protein are well known in the art and within the ordinary skill in the art. Techniques include salt fractionation, ion exchange chromatography, size exclusion chromatography, hydroxylapatite adsorption chromatography, hydrophobic interaction chromatography, immunoaffinity chromatography and affinity chromatography.

Mono-specific antibodies to human perlecan can be purified from mammalian antisera containing antibodies reactive against perlecan, or are prepared as monoclonal antibodies reactive with perlecan. Mono-specific antibody is defined as a single antibody species, or multiple antibody species with binding characteristics for perlecan, and includes polyclonal antibodies. Homogenous binding as used herein refers to the ability of the antibody species to bind to a specific antigen or epitope. Specific antibodies are raised by immunizing animals such as mice, rats, guinea pigs, rabbits, goats, horses and the like, with rabbits being preferred, with an appropriate concentration of perlecan, either with or without an immune adjuvant.

Preimmune serum is collected prior to the first immunization to establish baseline immunoreactivity. Each animal receives between about 0.1 mg and about 1000 mg of perlecan, either with or without an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of perlecan, and preferably Freund's complete adjuvant, at multiple sites either subcutaneously (SC), intraperitoneally (IP), or both. Each animal is bled at regular intervals, preferably weekly, to determine antibody titer. The animals may or may not receive booster injections following the initial immunization. Those animals receiving booster injections are generally given an equal amount of the initial antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20 degree C.

Monoclonal antibodies (mAb) reactive with perlecan are prepared by immunizing inbred mice, preferably Balb/c, with the appropriate antigen. The mice are immunized by the IP or SC route with about 0.1 mg to about 10 mg, preferably about 1 mg, of antigen in about 0.5 ml buffer or saline incorporated in an equal volume of an acceptable adjuvant, as discussed above. Freund's complete adjuvant is preferred. The mice receive an initial immunization on day 0 and are rested for about 2 to about 30 weeks. Immunized mice are given one or more booster immunizations of about 0.1 to about 10 mg of antigen in a buffer solution such as phosphate buffered saline by the subcutaneous or intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay using perlecan as the antigen. The culture fluids are also tested in the Ouchterlony precipitation assay and ELISA to determine the isotype of the mAb. Hybridoma cells from antibody positive wells are cloned by techniques well know in the art.

It is readily apparent to those skilled in the art that the above described methods for producing monospecific antibodies may be utilized to produce antibodies specific for the isolated perlecan, either alone or in combination with a modulating compound.

The antibodies produced above may be used as affinity columns by adding the antibodies to Affigel-10 (Biorad, Hercules, Calif.), according to the manufacturer's directions. After coupling of the antibodies to the column, the column is washed with water followed by 0.23M glycine HCl (pH 2.6) to remove any non-conjugated antibody or extraneous protein. The column is then equilibrated in phosphate buffered saline (pH 7.3) with appropriate detergent, and the cell culture supernatants or cell extracts containing perlecan, ether alone or in combination with a modulating compound, made using appropriate membrane solubilizing detergents are slowly passed through the column. The column is then washed with phosphate buffered saline/detergent until the optical density ($A_{280}$) falls to background, then the protein is eluted with 0.23M glycine-HCl (pH 2.6)/detergent. The purified protein is then dialyzed against phosphate buffered saline/detergent.

The present invention is also directed to methods for screening for compounds which modulate the expression of nucleic acid encoding perlecan, and/or the function of perlecan protein, in vivo and in vitro, either alone or in combination with a modulating compound. Compounds which modulate these activities may be DNA, RNA, peptides, proteins, or non-proteinaceous organic molecules. Compounds may modulate by increasing or attenuating the expression of DNA or RNA encoding perlecan or the function of the perlecan protein, either alone or in combination with a modulating compound. Compounds that modulate the expression of nucleic acid encoding perlecan, and/or the function of perlecan protein may be detected by a variety of assays. The assay may be a simple "yes/no" assay to determine whether there is a change in expression or function. The assay may be made quantitative by comparing the expression or function of a test sample with the levels of expression or function in a standard sample. The expression of perlecan protein, either alone or in combination with a modulating compound, is performed as described above. Such an assay is directed to direct inhibitors of perlecan nucleic acid expression or perlecan activity, as well as indirect inhibitors of this activity.

Kits containing perlecan nucleic acids or antibodies to perlecan may be prepared. Such kits can be used to detect nucleic acids which hybridize to the perlecan nucleic acids, or to detect the presence of perlecan protein or proteoglycan in a sample. In addition, such kits would contain the accessory reagents required to complete the assay contemplated by the kit.

Nucleotide sequences complementary to the nucleotide sequences coding for perlecan can be synthesized for antisense therapy. These antisense molecules may be DNA, stable derivatives of DNA such as phosphorothioates or methylphosphonates, RNA, stable derivatives of RNA such as 2'-O-alkylRNA, or other antisense oligonucleotide mimetics. These antisense molecules may be introduced into cells by microinjection, liposome encapsulation or by expression from vectors harboring the antisense sequence. Antisense therapy may be particularly useful for the treatment of diseases where it is beneficial to reduce perlecan activity.

Gene therapy may be used to introduce perlecan either alone or in combination with a modulating compound, into the cells. The nucleic acid coding for the appropriate protein can be ligated into viral vectors which mediate transfer of the DNA by infection of recipient host cells. Suitable viral vectors include retrovirus, adenovirus, adeno-associated virus, herpes virus, vaccinia virus, polio virus and the like. Alternatively, DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo gene therapy. Gene therapy may be particularly useful for the treatment of diseases where it is beneficial to elevate perlecan activity.

Pharmaceutically useful compositions comprising nucleic acids and their complements, and proteins corresponding to perlecan, either alone or in combination with modulating compounds, may be formulated according to known methods such as by the admixture of a pharmaceutically acceptable carrier. Examples of such carriers and methods of formulation may be found in *Remington's Pharmaceutical Sciences*. To form a pharmaceutically acceptable composition suitable for effective administration, such compositions will contain an effective amount of the protein, nucleic acid, or modulator compound.

Therapeutic or diagnostic compositions of the invention are administered to an individual in amounts sufficient to treat and/or diagnose disorders related to perlecan (defined as the "effective amount"). The effective amount may vary according to a variety of factors such as the individual's condition, weight, sex and age. Other factors include the mode or site of administration. The pharmaceutical compositions may be provided to the individual by a variety of routes such as subcutaneous, topical, oral, intraosseous, and intramuscular. Compounds identified according to the methods disclosed herein may be used alone at appropriate dosages defined by routine testing in order to obtain optimal activity, while minimizing any potential toxicity. In addition, co-administration or sequential administration of other agents may be desirable.

The therapeutic or diagnostic derivatives of perlecan discussed herein may be used with or without chemical derivatives. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences*.

The compositions containing compounds identified according to this invention as the active ingredient for use in the modulation of wound healing and/or angiogenesis can be administered in a wide variety of therapeutic dosage forms in conventional vehicles for administration. For example, the compounds can be administered in such forms as tablets, capsules (each including timed release and sustained release formulations), pills, powders, granules, elixirs, tinctures, solutions, suspensions, syrups, pastes and emulsions, or by injection internally.

In the present disclosure, the compounds herein described in detail can form the active ingredient, and are typically administered in admixture with suitable pharmaceutical diluents, excipients or carriers, which are collectively referred to herein as "carrier" materials, suitably selected with respect to the intended form of administration, that is, oral tablets, capsules, elixirs, syrups and the like, and consistent with conventional pharmaceutical practices. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like.

For oral forms, the active biologic component can be combined in suitably flavored suspending or dispersing agents such as the synthetic and natural gums, for example, tragacanth, acacia, methylcellulose and the like. Other dispersing agents that may be employed include glycerin and the like. For internal injection, sterile suspensions and solutions are desired. Isotonic preparations that generally contain suitable preservatives are employed when internal injection is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present disclosure may also be delivered by the use of monoclonal antibodies as individual carriers to which the compound molecules are coupled. The compounds of the present disclosure may also be coupled with soluble polymers as targetable drug carriers. Such polymers can include, but are not limited to, polyvinyl-pyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

All references to articles, books, patents, websites and other publications in this disclosure are considered incorporated by reference. The following examples illustrate certain embodiments of the present disclosure without, however, limiting the same thereto.

PROPHETIC EXAMPLES

Use of Perlecan in Surgical Procedures Including Periodontal Procedures

In one embodiment, perlecan would be purified from eukaryotic or bacterial cells via standard cell culture and protein purification methodology. Exemplary cell types, cell growth conditions and antibodies for affinity purification of perlecan from cultured eukaryotic cells have been described (2, 16, 21, 22, 39). Eukaryotic cells may be from primary culture or may be derived from cloned or immortalized cell lines (8, 10, 20). Antibody affinity chromatography may be used to purify perlecan from either cell source (25, 34). Various monoclonal antibodies that are specific for different epitopes of perlecan are available commercially and could be used in sequence to optimize purity. Purity would be established by molecular sieve chromatography and SDS-PAGE electrophoresis, or by other standard techniques (17). Purification of perlecan may be from cell culture media directly, or may involve fractionation of cells by standard methods and purification, such as isolation of and purification from intracellular inclusion bodies (26). Once released from inclusion bodies by standard techniques, affinity purification would follow as described above. Cloning of perlecan would involve standard PCR and ligation procedures into any number of suitable eukaryotic or bacterial expression vectors (6). Importantly, when perlecan is expressed in bacteria, it may be necessary to alter the nucleic acid sequence of perlecan to meet the requirements of the transcriptional and translation system of the bacterial host. These forms of perlecan, and the nucleic acid sequences coding for them, are included in the definition of perlecan derivative.

As discussed above, perlecan would include those with different sulfation patterns and differing amounts of glycosaminoglycan chains. The presence or absence of particular modifications may differ between eukaryotic and bacterial cells, and within different cells types within each class. In addition, perlecan may be administered with or without various growth factors. As discussed above, perlecan has been shown to bind certain growth factors and may play a role in regulating the activity of these growth factors. Therefore, it may be advantageous to administer perlecan with growth factors in certain situations. It is preferred that the perlecan is mixed with the growth factor prior to being incorporated into a pharmaceutically acceptable formulation. The molar ratio of perlecan to growth factor can range from 0.1 to 1 to 20 to 1, but a preferred ration is 1 to 1. Growth factors that may be used with perlecan include, but are not limited to, members of the fibroblast growth factor family, such as FGF-2 and FGF-7, and GM-CSF. Other growth factors determined to be active in either wound healing, tissue remodeling or angiogenesis may also be used with perlecan.

Perlecan may be incorporated into various pharmaceutically acceptable formulations for use as discussed above. In one embodiment perlecan may be mixed with a carrier paste. Various carrier pastes for dermal or surgical application are available and many are inert formulations based on cellulose. Perlecan is included in the paste at an effective concentration as discussed above. In one embodiment, the range of perlecan concentrations within the carrier paste is 1 pM to 1 µM. The perlecan (preferably in a pharmaceutically acceptable formulation, such as the paste described above) may be used during a variety of purposes. For example, during periodontal procedures, perlecan may be applied at the time of surgical closure between and below flaps. Approximately 1 ml of paste containing perlecan would be applied for every 6 $cm^2$ of wound surface, and would be applied liberally.

A variety of systems have been developed to accomplish expression of exogenous proteins via the delivery of nucleic acid sequences coding for the given protein into target cells. In one embodiment, perlecan would be delivered as an adjunct to wound healing or surgical healing by placing into the wound or surgical site cells which have been induced to express perlecan. These cells would have preferably been derived from the recipient, but may be of an allograft or xenograft nature, being derived from other human donors, or from animals. Cells may include stem cells, endothelial cells, epithelial cells, fibroblasts, monocytes or macrophages. The target cells will be collected from the blood or tissues of the donor by standard methods and nucleic acid coding for perlecan will be introduced into the cell. Methods of introducing the perlecan encoding nucleic acid into cells are well known in the art as described above. One such method involves infecting the target cells with a viral-based expression vector, such as adenovirus. Adenovirus containing perlecan encoding nucleic acid and target cells are mixed for 30 minutes in serum-free cell culture media. After this infection period, the cells will be collected by centrifugation and applied to the wound or surgical site at a density of between $10^3$-$10^6$ cells per $cm^2$.

In another embodiment, a nucleic acid fragment coding for perlecan would be delivered to the desired site in a viral-based expression vector. There are many choices for viral-based expression vectors which are well known in the art. However, a preferred viral vector is the adenovirus. There are several good reasons for utilizing recombinant adenovirus vectors for the delivery of nucleic acid encoding perlecan. First, stocks of adenovirus containing high titers of virus (greater than $10^{11}$ pfu per ml) can be prepared, which makes it possible to transduce cells in situ at high multiplicity of infection for high localized protein production. Also, the adenovirus is capable of inducing high levels of transgene expression, at least as an initial burst. Third, the vector can be engineered to incorporate a high degree of versatility. Finally, the adenovirus vector is safe based on its long-term use as a vaccine. Recombinant adenovirus vectors have been utilized as vaccine carriers by intranasal, intratracheal, intraperitoneal, intravenous, subcutaneous, or intramuscular routes (9, 12, 18). In this embodiment, nucleic acid encoding perlecan, such as cDNA will be ligated into a replication-incompetent, E1/E3-defective human adenovirus serotype 5-derived vector under the transcriptional control of the human cytomegalovirus early promoter as described previously (41). For inducing perlecan expression from said cDNA expression system, $10^5$ to $10^9$ adenovirus particles will be delivered per $cm^2$ of wound surface area, or per $cm^3$ of a surgical grafting site.

The exogenous perlecan encoding nucleic acid may also be incorporated into the pharmaceutically acceptable carriers described above for the uses discussed above. For example, perlecan encoding nucleic acid may be incorporated into a paste formulation as discussed above and used in surgical and periodontal procedures, such as flap surgery, or applied to cutaneous injuries, such as burns or cuts. In addition, perlecan encoding nucleic acids may be applied to grafting materials, implant materials, surgical barrier membranes and dressings for the purposes described below. As an example, perlecan encoding nucleic acid may be adsorbed onto the surface of an implant before implant placement by painting, spraying, or soaking the implant material in a sterile solution of exogenous perlecan encoding nucleic acid for periods of time ranging from 1 second to 24 hours.

Use of Perlecan for Cutaneous Injury

In this embodiment, perlecan is expressed and purified as discussed above. As discussed in Example 1, perlecan may be used in a variety of forms and in a variety of pharmaceutically acceptable formulations. As another example of perlecan use, perlecan may be applied to the surface of a site of cutaneous injury, such as a burn, a non-healing ulcer, or a cut or similar injury. Approximately 1 ml of paste containing perlecan would be applied for every 6 $cm^2$ of wound surface and would be applied liberally. In addition, the perlecan-containing paste may be delivered in association with a bandage or other dressing applied to the site of injury.

Use of Perlecan in Conjunction with Surgical Implants and Similar Materials

In this embodiment, perlecan is expressed and purified as discussed above. As discussed in Example 1, perlecan may be used in a variety of forms and in a variety of pharmaceutically acceptable formulations. As another example of perlecan use, perlecan may be applied to and absorbed on the surface of surgical implants, grafting material or barrier membranes.

Surgical implants include, but are not limited to, those made of titanium or titanium coated with hydroxy-apatite material. Bone grafting materials include, but are not limited to, hydroxyl apatite in various crystal sizes and forms, and autologous, autogenous, or xenograft donor bone, either cortical or cancellous, and freeze-dried with demineralization. Barrier membrane materials include, but are not limited to, poly vinyl difluoride (Gore-Tex), poly galactic acid, or collagen (BioMend). The surgical implants, grafting materials and barrier membrane would be pre-treated in a solution of perlecan, approximately 1 pM to 1 µM in concentration, preferably in a sterile buffer such as phosphate buffer, pH 7.4. The pre-treatment may be performed during surgery, or at any time prior to the surgery provided the coated surgical implant material is not subject to temperatures above 37° C. at any time. The pre-treatment procedure would involve immersion in the perlecan solution for at least 10 seconds, preferably 5 minutes. The treated membrane would then be surgically placed. As discussed above, various growth factors may also be incorporated into the perlecan solution for incorporation into and absorption onto the surgical implants, grafting materials and barrier membranes. Once prepared, the surgical implants, grafting materials and barrier membranes are used according to standard procedures.

REFERENCES

1. Andriesson M P, van den Born J, Latijnhouwers M A, Bergers M, van de Kerkhof P C, Schalkwijk J. Basal membrane heparan sulphate proteoglycan expression during wound healing in human skin. J. Pathol. 1997:183:251-252
2. Aviezer D, Hecht D, Safran M, Eisinger M, David G, Yayon A. Perlecan, basal lamina proteoglycan, promotes basic fibroblast growth factor-receptor binding, mitogenesis, and angiogenesis. Cell 1994:79:1005-1013
3. Aviezer D, Iozzo R V, Noonan D M, Yayon A. Suppression of autocrine and paracrine functions of basic fibroblast growth factor by stable expression of perlecan antisense cDNA. Mol. Cell. Biol. 1997:17: 1938-1946
4. Battaglia C, Aumailley M, Mann K, Mayer U, Timpl R. Structural basis of beta-1 integrin-mediated cell adhesion to a large heparan sulfate proteoglycan from basement membranes. Eur. J. Cell Biol. 1993:61:92-99
5. Brown J C, Sasaki T, Gohring W, Yamada Y, Timpl R. The C-terminal domain V of perlecan promotes beta1 integrin-mediated cell adhesion, binds heparin, nidogen and fibulin-2 and can be modified by glycosaminoglycans. Eur. J. Biochem. 1997:250:39-46
6. Burke J F. PCR: essential techniques. Ed. Burke, J. F. New York: Wiley, 1996: 168.
7. Carson D D, Tang J P, Julian J. Heparan sulfate proteoglycan (perlecan) expression by mouse embryos during acquisition of attachment competence. Dev. Biol. 1993:155:97-106
8. Chakravarti S, Horchar T, Jefferson B, Laurie G W, Hassell J R. Recombinant domain III of perlecan promotes cell attachment through its RGDS sequence. J. Biol. Chem. 1995:270:404-409
9. Chen H H, Mack L M, Kelly R, Ontell M, Kochanek S, Clemens P R. Persistence in muscle of an adenoviral vector that lacks all viral genes. Proc. Natl. Acad. Sci. USA 1996: 94:1645-1650
10. Costell M, Mann K, Yamada Y, Timpl R. Characterization of recombinant perlecan domain I and its substitution by glycosaminoglycans and oligosaccharides. Eur. J. Biochem. 1997:243:115-121
11. Costell M, Sasaki T, Mann K, Yamada Y, Timpl R. Structural characterization of recombinant domain II of the basement membrane proteoglycan perlecan. FEBS Letters 1996:396:127-131
12. Croyle M A, Anderson D J, Foessler B J, Amidon G L. Development of a highly efficient purification process for recombinant adenoviral vectors for oral gene delivery. Pharmaceutical Development Technology 1998:3:365-372
13. Dodge G R, Boesler E W, Jimenez S A. Expression of the basement membrane heparan sulfate proteoglycan (perlecan) in human synovium and in cultured human synovial cells. Lab. Investig. 1995:73:649-657
14. Dolan M, Horchar T, Rigatti B, Hassel JR. Identification of sites in domain I of perlecan that regulate heparan sulfate synthesis. J. Biol. Chem. 1997:272:4316-4322
15. Fuki I V, Iozzo R V, Williams K J. Perlecan heparan sulfate proteoglycan: a novel receptor that mediates a distinct pathway for ligand catabolism. J. Biol. Chem. 2000:275: 25742-25750
16. Gauer S, Schulzelohoff E, Schleicher E, Sterzel R B. Glomerular basement membrane-derived perlecan inhibits mesangial cell adhesion to fibronectin. Eur. J. Cell Biol. 1996:70:233-242
17. Gersten D M. Gel electrophoresis: proteins essential techniques. Ed. Gersten, D. M. New York: Wiley Publishing, 1996: 192.
18. Gomez-Foix A M, Coats W S, Baque S, Alam T, Gerard R D, Newgard C B. Adenovirus-mediated transfer of the muscle glycogen phosphorylase gene into hepatocytes confers altered regulation of glycogen metabolism. J. Biol. Chem. 1992:267:25129-25134
19. Graham L D, Whitelock J M, Underwood P A. Expression of human perlecan domain I as a recombinant heparan sulfate proteoglycan with 20-kDa glycosaminoglycan chains. Biochem. Biophys. Res. Comm. 1999:256:542-548
20. Groffen A J A, Buskens C A F, Tryggvason K, Veerkamp J H, Monnens L A H, Vandenheuvel L P W J. Expression and characterization of human perlecan domains I and II synthesized by baculovirus-infected insect cells. Eur. J. Biochem. 1996:241:827-834
21. Hagen S G, Michael A F, Butkowski R J. Immunochemical and biochemical evidence for distinct basement membrane heparan sulfate proteoglycans. J. Biol. Chem. 1993: 268:7261-7269
22. Hassell J R, Robey P G, Barrach H-J, Wilczek J, Rennard S I, Martin G R. Isolation of a heparan sulfate-containing proteoglycan from basement membrane. Proc. Natl. Acad. Sci. USA 1980: 77:
23. Hayashi K, Madri J A, Yurchenco P D. Endothelial cells interact with the core protein of basement membrane perlecan through beta1 and beta3 integrins—an adhesion modulated by glycosaminoglycan. J. Cell Biol. 1992:119: 945-959
24. Hopf M, Gohring W, Kohfeldt E, Yamada Y, Timpl R. Recombinant domain IV of perlecan binds to nidogens, laminin-nidogen complex, fibronectin, fibulin-2 and heparin. Eur. J. Biochem. 1999:259:917-925
25. Janson J-C, Ryden L. Protein purification: principles, high-resolution methods, and applications. Ed. Jansen, J.-C., and Ryden, L. New York: Wiley, 1998: 712.
26. Jones P. Vectors: expression systems: essential techniques. Ed. Jones, P. New York: Wiley, 1998:168.
27. Kasinath B S, Grellier P, Choudhury G G, Abboud S L. Regulation of basement membrane heparan sulfate proteoglycan, perlecan, gene expression in glomerular epithelial cells by high glucose medium. J. Cell Physiol. 1996: 167:131-136
28. Klein G, Conzelmann S, Beck S, Timpl R, Muller C A. Perlecan in human bone marrow: a growth-factor-presenting, but anti-adhesive, extracellular matrix component for hematopoietic cells. Matrix Biol. 1995:14:457-465

29. Larjava H, Hakkinen L, Rahemtulla F. A biochemical analysis of human periodontal tissue proteoglycans. Biochem. J. 1992:284:267-274
30. Mongiat M, Otto J, Oldershaw R, Ferrer F, Sato J D, Iozzo R V. Fibroblast growth factor-binding protein is a novel partner for perlecan protein core. J. Biol. Chem. 2001:30: 10263-10271
31. Mongiat M, Taylor K, Otto J, Aho S, Uitto J, Whitelock J M, Iozzo R V. The protein core of the proteoglycan perlecan binds specifically to fibroblast growth factor-7. J. Biol. Chem. 2000: 275: 7095-7100
32. Murdoch A D, Dodge G R, Cohen I, Tuan R S, Iozzo R V. Primary structure of the human heparan sulfate proteoglycan from basement membrane (HSPG2/perlecan)—a chimeric molecule with multiple domains homologous to the low density lipoprotein receptor, laminin, neural cell adhesion molecules, and epidermal growth factor. J. Biol. Chem. 1992:267:8544-8557
33. Murdoch A D, Liu B, Schwarting R, Tuan R S, Iozzo R V. Widespread expression of perlecan proteoglycan in basement membranes and extracellular matrices of human tissues as detected by a novel monoclonal antibody against domain III and by in situ hybridization. J. Histochem. Cytochem 1994:42:239-249
34. Myers R. Immunology: A Laboratory Manual. Ed. McGraw-Hill Science, 1994: 144.
35. Nissen N N, Shankar R, Gamelli R L, Singh A, DiPietro L A. Heparin and heparan sulphate protect basic fibroblast growth factor from non-enzymic glycosylation. Biochem. J. 1999:338:637-642
36. Noonan D M, Fulle A, Valente P, Cai S, Horigan E, Sasaki M, Yamada Y, Hassell J R. The complete sequence of perlecan, a basement membrane heparan sulfate proteoglycan, reveals extensive similarity with laminin A chain, low density lipoprotein-receptor, and the neural cell adhesion molecule. J. Biol. Chem. 1991: 266(34): 22939-22947
37. Nugent M A, Iozzo R V. Fibroblast growth factor-2. Int. J. Biochem. Cell Biol. 2000:32:115-120
38. Oksala O, Salo T, Tammi R, Hakkinen L, Jalkanen M, Inki P, Larajava H. Expression of proteoglycans and hyaluronan during wound healing. J. Histochem. Cytochem 1995:43: 125-135
39. Saku T, Furthmayr H. Characterisation of the major heparan sulfate proteoglycan secreted by bovine aortic endothelial cells in culture. J. Biol. Chem. 1989:264:3514-3523
40. Sharma B, Handler M, Eichstetter I, Whitelock J M, Nugent M A, Iozzo R V. Antisense targeting of perlecan blocks tumor growth and angiogenesis in vivo. J. Clin. Invest. 1998: 102: 1599-1608
41. Shi Z, Zeng M, Yang G, Seigel F, Cain L J, van Kampen K R, Elmets C A, Tang D-C C. Protection against tetanus by needle-free inoculation of adenovirus-vectored nasal and epicutaneous vaccines. Journal of Virology 2001:75: 11474-11482
42. Sundarraj N, Fite D, Belak R, Sudarraj S, Rada J, Okamoto S, Hassell J. Proteoglycan distribution during healing of corneal stromal wounds in chick. Exp. Eye Res. 1998: 67:433-442
43. Sundarraj N, Fite D, Ledbetter S, Chakravarti S, Hassell JR. Perlecan is a component of cartilage matrix and promotes chondrocyte attachment. J. Cell Sci. 1995:108: 2663-2672
44. Tolsma S S, Stack M S, Bouck N. Lumen formation and other angiogenic activities of cultured capillary endothelial cells are inhibited by thrombospondin-1. Microvasc. Res. 1997:54:13-26
45. Vischer P, Feitsma K, Schon P, Volker W. Perlecan is responsible for thrombospondin 1 binding on the cell surface of cultured porcine endothelial cells. Eur. J. Cell Biol. 1997:73:332-343
46. Whitelock J M, Graham L D, Melrose J, Iozzo R V, Underwood P A. Human perlecan immunopurified from different endothelial cell sources has different adhesive properties for vascular cells. Matrix Biol. 1999:18:163-178
47. Whitelock J M, Murdoch A D, Iozzo R V, Underwood P A. The degradation of human endothelial cell-derived perlecan and release of bound basic fibroblast growth factor by stromelysin, collagenase, plasmin, and heparanases. J. Biol. Chem. 1996:271:10079-10086
48. Yu W H, Woessner J F, Jr. Heparan sulfate proteoglycans as extracellular docking molecules for matrilysin (matrix metalloproteinase 7). J. Biol. Chem. 2000:275:183-191

What is claimed:

1. A method for the effective healing of a wound or a cutaneous injury in a subject in need of such healing via delivery of a heparin sulfate-decorated perlecan molecule, the method comprising administering to the wound or cutaneous injury in the subject a nucleic acid coding for perlecan whereby said heparin sulfate-decorated perlecan molecule is generated by the subject, said nucleic acid being delivered in an amount sufficient to deliver an effective amount of heparin sulfate-decorated perlecan to the wound or cutaneous injury resulting in an in improvement in healing of the wound or cutaneous injury in the subject.

2. The method of claim 1 where the nucleic acid has the sequence of SEQ ID NO. 5.

3. The method of claim 1 where the nucleic acid codes for an amino acid having the sequence of SEQ ID NO. 4.

4. The method of claim 1 where the nucleic acid is a fragment of SEQ ID NO. 5.

5. The method of claim 4 where said fragment is at least 150 nucleotides in length and is selected from nucleotides 1-600 of SEQ ID NO. 5.

6. The method of claim 4 where said fragment codes for at least 50 amino acids selected from amino acids 1-172 of SEQ ID NO. 4.

7. The method of claim 4 where said fragment codes for amino acids 1-172 of SEQ ID NO. 4.

8. The method of claim 1 where said nucleic acid is delivered in a pharmaceutically acceptable carrier or diluent.

9. The method of claim 1 further comprising the administration of a modulating compound.

10. A method for the effective healing of a wound or a cutaneous injury in a subject in need of such healing via delivery of a heparin sulfate-decorated perlecan molecule, the method comprising administering to the wound or cutaneous injury in the subject a nucleic acid that is at least 70% identical to the nucleic sequence of SEQ ID NO. 5 whereby said heparin sulfate-decorated perlecan molecule is generated by the subject, said nucleic acid being delivered in an amount sufficient to deliver an effective amount of heparin sulfate-decorated perlecan to the wound or cutaneous injury resulting in an in improvement in healing of the wound or cutaneous injury in the subject.

11. The method of claim 10 where said nucleic acid is delivered in a pharmaceutically acceptable carrier or diluent.

12. The method of claim 10 further comprising the administration of a modulating compound.

13. A method for the effective healing of a wound or a cutaneous injury in a subject in need of such healing via delivery of a heparin sulfate-decorated perlecan molecule, the method comprising administering to the wound or cutaneous injury in the subject a nucleic acid that codes for a protein that is at least 70% identical to the amino acid sequence of SEQ ID NO. 4 whereby said heparin sulfate-decorated perlecan molecule is generated by the subject, said nucleic acid being delivered in an amount sufficient to deliver an effective amount of heparin sulfate-decorated perlecan to the wound or cutaneous injury resulting in an in improvement in healing of the wound or cutaneous injury in the subject.

14. The method of claim 13 where said nucleic acid is delivered in a pharmaceutically acceptable carrier or diluent.

15. The method of claim 13 further comprising the administration of a modulating compound.

* * * * *